(12) United States Patent
Okazoe et al.

(10) Patent No.: US 7,083,705 B2
(45) Date of Patent: *Aug. 1, 2006

(54) PROCESS FOR PRODUCING A FLUORINE-CONTAINING COMPOUND BY LIQUID PHASE FLUORINATION

(75) Inventors: Takashi Okazoe, Yokohama (JP); Kunio Watanabe, Yokohama (JP); Shin Tatematsu, Yokohama (JP); Hidenobu Murofushi, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/915,423

(22) Filed: Aug. 11, 2004

(65) Prior Publication Data

US 2005/0020855 A1    Jan. 27, 2005

Related U.S. Application Data

(63) Continuation of application No. 10/421,924, filed on Apr. 24, 2003, now Pat. No. 6,961,957, which is a continuation of application No. 09/960,381, filed as application No. PCT/JP00/01765 on Mar. 23, 2000, now Pat. No. 6,586,626.

(30) Foreign Application Priority Data

Mar. 23, 1999 (JP) .................................. 11-078544
Aug. 31, 1999 (JP) .................................. 11-246154

(51) Int. Cl.
C07C 51/04 (2006.01)

(52) U.S. Cl. ................... 204/157.89; 562/851; 562/852

(58) Field of Classification Search ................ 562/851, 562/852; 204/157.89
See application file for complete search history.

(56) References Cited

U.S. PATENT DOCUMENTS

| | | | |
|---|---|---|---|
| 3,900,372 A | 8/1975 | Childs et al. |
| 4,524,032 A | 6/1985 | Misaki et al. |
| 4,868,318 A | 9/1989 | Scherer et al. |
| 4,996,369 A | 2/1991 | Kalota et al. |
| 5,093,432 A | 3/1992 | Bierschenk et al. |
| 5,322,903 A | 6/1994 | Bierschenk et al. |
| 5,466,877 A | 11/1995 | Moore |
| 5,488,142 A | 1/1996 | Fall et al. |
| 5,571,870 A | 11/1996 | Bierschenk et al. |
| 5,578,278 A | 11/1996 | Fall et al. |
| 5,674,949 A | 10/1997 | Bierschenk et al. |
| 5,753,776 A | 5/1998 | Bierschenk et al. |
| 6,093,860 A | 7/2000 | Watanabe et al. |
| 6,166,125 A | 12/2000 | Sugiyama et al. |
| 6,255,536 B1 | 7/2001 | Worm et al. |
| 6,747,174 B1 | 6/2004 | Okazoe et al. |
| 2002/0107358 A1 | 8/2002 | Okazoe et al. |
| 2003/0135067 A1 | 7/2003 | Okazoe et al. |
| 2003/0139570 A1 | 7/2003 | Okazoe et al. |
| 2003/0166969 A1 | 9/2003 | Okazoe et al. |
| 2003/0216595 A1 | 11/2003 | Okazoe et al. |
| 2004/0110968 A1 | 6/2004 | Okazoe et al. |
| 2004/0204618 A1 | 10/2004 | Okazoe et al. |

FOREIGN PATENT DOCUMENTS

| | | |
|---|---|---|
| EP | 265052 | 4/1988 |
| EP | 0 557 167 A1 | 8/1993 |
| EP | 1 208 075 A1 | 5/2002 |
| JP | 10-116627 | 5/1998 |
| WO | WO 00/56694 | 9/2000 |
| WO | WO 01/16085 | 3/2001 |
| WO | WO 01/46093 | 6/2001 |
| WO | WO 01/46107 | 6/2001 |
| WO | WO 01/94285 | 12/2001 |
| WO | WO 02/04397 | 1/2002 |
| WO | WO 02/10106 | 2/2002 |
| WO | WO 02/10107 | 2/2002 |
| WO | WO 02/10108 | 2/2002 |
| WO | WO 02/18314 | 3/2002 |
| WO | WO 02/20445 | 3/2002 |
| WO | WO 02/26679 | 4/2002 |
| WO | WO 02/26682 | 4/2002 |
| WO | WO 02/26686 | 4/2002 |
| WO | WO 02/26687 | 4/2002 |
| WO | WO 02/26688 | 4/2002 |
| WO | WO 02/26689 | 4/2002 |
| WO | WO 02/26693 | 4/2002 |

OTHER PUBLICATIONS

Murata et al., "The Thermal Decomposition of Perfluoroesters", J. Am. Chem. Soc., 1998, vol. 120, No. 28, pp. 7117-7118.

Tari Isao et al., "Synthesis of Halogenated Esters of Flurinaterd Carboxylic Acids by the Regio- and Stereospecific Addition of Acyl Hypochlorites to Olefins", J. Org. Chem., 1980, vol. 45, No. 7, p. 1214-1217.

*Primary Examiner*—Bernard Dentz
(74) *Attorney, Agent, or Firm*—Oblon, Spivak, McClelland, Maier & Neustadt, P.C.

(57) ABSTRACT

The invention provides a process for producing a fluorine-containing compound from an inexpensive material.

Namely, Compound I such as $R^A CH_2 OH$ is reacted with Compound II such as $XCOR^B$ to form Compound III such as $R^A CH_2 OCOR^B$, followed by fluorination in a liquid phase to form Compound IV such as $R^{AF} CF_2 OCOR^{BF}$, which is converted to Compound V such as $R^{AF} COF$ and/or Compound VI such as $R^{BF} COF$. $R^A$ is an alkyl group or the like, $R^B$ is a perhalogenoalkyl group or the like, $R^{AF}$ and $R^{BF}$ are fluorinated $R^A$ and $R^B$, and X is halogen.

16 Claims, No Drawings

PROCESS FOR PRODUCING A FLUORINE-CONTAINING COMPOUND BY LIQUID PHASE FLUORINATION

CROSS-REFERENCE TO RELATED APPLICATIONS

The present application is a continuation of application Ser. No. 10/421,924 filed Apr. 24, 2003 now U.S. Pat. No. 6,951,957, which is a continuation of application Ser. No. 09/960,381 filed Sep. 24, 2001, now U.S. Pat. No. 6,586,626 which is the National Stage of International Application No. PCT/JP00/01765 filed Mar. 23, 2000.

TECHNICAL FIELD

The present invention relates to a process for producing a fluorine-containing compound such as an industrially useful acid fluoride compound. Further, the present invention provides a novel compound which is useful as a precursor for a fluorine resin material.

BACKGROUND ART

Heretofore, as a method for fluorinating all of C—H portions in a C—H containing compound to C—F, a method of employing cobalt trifluoride, a method of direct fluorination with fluorine gas, or a method of carrying out a fluorination reaction in an electrolytic cell using electrolyzed hydrogen fluoride as a fluorine source (hereinafter referred to as electrochemical fluorination) has been known. The method of employing cobalt trifluoride is one wherein the reaction is carried out at a high temperature by a gas-solid reaction, whereby isomerization or bond breakage takes place, and there is a problem that various types of by-products will form. In the case where a direct fluorination method is carried out with fluorine gas, a gas phase method or a liquid phase method has been known. However, the gas phase reaction has a problem that during the fluorination reaction, dissociation of C—C single bonds takes place, and various types of by-products will form. In recent years, a liquid phase method has been reported.

On the other hand, a method for fluorination in a liquid phase by reacting fluorine gas to a non-fluorine containing compound, has also been reported (U.S. Pat. No. 5,093,432). Further, a method for obtaining an acid fluoride compound by thermal decomposition of a perfluorinated ester compound having a carbon number of at least 16, has also been known, and it is disclosed that the compound can be obtained by direct fluorination of a hydrocarbon ester compound having a corresponding structure in a liquid phase with fluorine gas (J. Am. Chem. Soc., 120, 7117 (1998)).

The method of employing cobalt trifluoride or electrochemical fluorination has had a problem such that an isomerization reaction takes place or a problem such that breakage of the main chain, a re-union reaction, etc., may occur, and has had a drawback that the desired compound can not be obtained in good purity. In a case where a fluorination reaction is carried out in a liquid phase with fluorine gas, it is common to employ a solvent capable of dissolving fluorine gas, as the solvent for the reaction. However, a hydrocarbon compound as a starting material in a conventional method, usually has a low solubility in a solvent to be used for the fluorination reaction, and accordingly, the reaction is carried out in a very low concentration, whereby there has been a problem that the production efficiency is poor or a problem that the reaction will have to be carried out in a suspension which is disadvantageous to the reaction. Further, if it is attempted to fluorinate a hydrocarbon compound of a low molecular weight in a liquid phase, a problem has been observed such that the reaction yield tends to be remarkably low.

On the other hand, a fluorine-containing monomer such as a perfluoro(alkylvinyl ether) is useful as a starting material monomer for a fluorinated resin having heat resistance and chemical resistance. Heretofore, the perfluoro(alkylvinyl ether) has been industrially produced by a dimerization reaction of a perfluorinated epoxide or by reacting a perfluoroalkanoyl fluoride with a perfluorinated epoxide in the presence of an alkali metal fluoride to form a perfluoro(2-alkoxyalkanoyl)fluoride, followed by thermal decomposition. However, such a method has had a problem that control of the reaction of the dimerization reaction is difficult, and the price of the starting material is high and economically disadvantageous.

DISCLOSURE OF THE INVENTION

In the present invention, as a result of various studies on the cause for problems of the conventional methods, firstly, it has been found that the cause for the low yield in the fluorination reaction in a liquid phase with fluorine gas, is attributable to the fact that if the boiling point of the starting material is low, the starting material will react in a gas phase so that a decomposition reaction takes place. Then, it has been found that the decomposition reaction can be prevented by using an inexpensively available C—H containing compound as the starting material, converting it to a compound of a specific structure which has a high molecular weight so that a gas phase reaction hardly takes place and which is soluble in a solvent for the fluorination reaction, followed by fluorination in a liquid phase. Further, it has been found that the desired fluorine-containing compound can be produced by dissociation of a bonded group after fluorination (for example, dissociation by means of a thermal decomposition reaction or a decomposition reaction carried out in the presence of a nucleophile or an electrophile). Further, an industrial continuous process by recycling the formed compound, has been found.

Namely, the present invention provides a process for producing a fluorine-containing compound, characterized by reacting the following compound (I) with the following compound (II) to form the following compound (III), fluorinating the compound (III) in a liquid phase to form the following compound (IV) and then converting the compound (IV) to the following compound (V) and/or the following compound (VI):

  (I)

  (II)

  (III)

  (IV)

  (V)

  (VI)

wherein $R^A$, $R^B$: each independently is a monovalent saturated hydrocarbon group, a halogeno monovalent saturated hydrocarbon group, a hetero atom-containing monovalent saturated hydrocarbon group, a halogeno(hetero atom-containing monovalent saturated hydrocarbon) group, or a monovalent organic group ($R^H$) which can be converted to $R^{HF}$ by a liquid-phase fluorination reaction, $R^{HF}$: a group having at least one hydrogen atom in a group selected from a monovalent saturated hydrocarbon group, a partially halogeno monovalent saturated hydrocarbon group, a hetero atom-containing monovalent saturated hydrocarbon group, and a partially halogeno (hetero atom-containing monovalent hydrocarbon) group, substituted by a fluorine atom;

$R^{AF}$, $R^{BF}$: $R^{AF}$ is a group corresponding to $R^A$, and $R^{BF}$ is a group corresponding to $R^B$; and in a case where each of $R^A$ and $R^B$ is a monovalent saturated hydrocarbon group, a halogeno monovalent saturated hydrocarbon group, a hetero atom-containing monovalent saturated hydrocarbon group, or a halogeno (hetero atom-containing saturated hydrocarbon) group, $R^{AF}$ and $R^{BF}$ are the same groups as $R^A$ and $R^B$, respectively, or groups having at least one fluorine atom present in the groups of $R^A$ and $R^B$ substituted by a fluorine atom, and in a case where $R^A$ and $R^B$ are monovalent organic groups ($R^H$), $R^{AF}$ and $R^{BF}$ are $R^{HF}$, respectively;

$E^1$, $E^2$: reactive groups which are mutually reactive to form a bivalent connecting group (E);

E: a bivalent connecting group formed by the reaction of $E^1$ and $E^2$;

$E^F$: the same group as E, or a group having E fluorinated, provided that at least one of $R^{AF}$, $R^{BF}$ and $E^F$, is not the same group as the corresponding $R^A$, $R^B$ and E, respectively;

$E^{F1}$, $E^{F2}$: each independently is a group formed by dissociation of $E^F$.

Further, the present invention provides the following novel compounds, provided that in this specification, Cy is a cyclohexyl group, Ph is a phenyl group, and $Cy^F$ is a perfluoro(cyclohexyl) group;

$CF_3(CF_3CF_2F_2O)CFCOOCH_2CH(OCH_2CH_2CH_3)CH_3$,
$CF_3CF_2COOCH_2CH_2CHClCH_2Cl$,
$CF_2ClCFClCF_2COOCH_2CH_2CHClCH_2Cl$,
$CF_2ClCF_2CFClCOOCH_2CH_2CHClCH_2Cl$,
$CF_3(CF_3CF_2CF_2O)CFCOOCH_2CH$
$(OCH_2CH_2CHClCH_2Cl)CH_3$,
$CF_3(CF_3CF_2CF_2O)CFCOOCH_2CH(OCH_2Cy)CH_3$,
$CF_3(CF_3CF_2CF_2O)CFCOOCH_2CH(OCH_2Ph)CH_3$,
$CF_3(CF_3CF_2CF_2O)CFCOOCH_2CH(O(CH_2)_9CH_3)CH_3$,
$CF_3(CF_3CF_2CF_2O)CFCOO(CH_2)_3OCH_2Ph$,
$CF_3(CF_3CF_2CF_2O)CFCOO(CH_2)_3OCH_2CH=CH_2$,

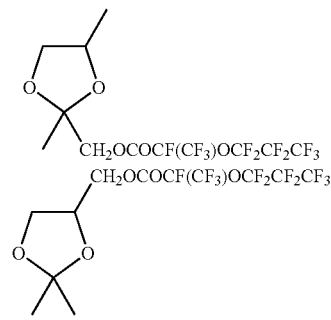

$CF_3(CF_3CF_2CF_2O)CFCOOCF_2CF(OCF_2CF_2CF_3)CF_3$,
$CF_3CF_2COOCF_2CF_2CF_3$,
$CF_3CF_2COOCF_2CF_2CFClCF_2Cl$,
$CF_2ClCFClCF_2COOCF_2CF_2CFClCF_2Cl$,
$CF_2ClCF_2CFClCOOCF_2CF_2CFClCF_2Cl$,
$CF_3(CF_3CF_2CF_2O)CFCOOCF_2CF$
$(OCF_2CF_2CFClCF_2Cl)CF_3$, $CF_3(CF_3CF_2CF_2O)CFCOOCF_2CF(OCF_2Cy^F)CF_3$,
$CF_3(CF_3CF_2CF_2O)CFCOOCF_2CF(O(CF_2)_9CF_3)CF_3$,
$CF_3(CF_3CF_2CF_2O)CFCOO(CF_2)_3OCF_2Cy^F$,
$CF_3(CF_3CF_2CF_2O)CFCOO(CF_2)_3OCF_2CF_2CF_3$,

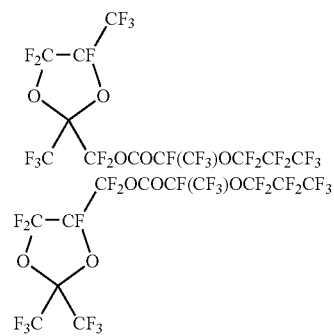

$FCOCF(O(CF_2)_9CF_3)CF_3$
$FCO(CF_2)_2OCF_2Cy^F$.

BEST MODE FOR CARRYING OUT THE INVENTION

Description of Groups Disclosed in the Specification

In the present specification, a monovalent organic group means a monovalent group which essentially comprises carbon atoms. The monovalent organic group may or may not contain fluorine atoms or hydrogen atoms. The carbon number of the monovalent organic group is preferably from 1 to 20, particularly preferably from 1 to 10, from the viewpoint of the solubility in a liquid phase at the time of the fluorination reaction.

In the present specification, the monovalent hydrocarbon group may be a monovalent aliphatic hydrocarbon group or a monovalent aromatic hydrocarbon group, and a monovalent aliphatic hydrocarbon group is preferred. The structure of the monovalent aliphatic hydrocarbon group may, for example, be a straight chain structure, a branched structure, a cyclic structure or a structure having a partially cyclic structure. In the monovalent aliphatic hydrocarbon group, a single bond, a double bond or a triple bond may be present as a carbon-carbon bond. When the monovalent aliphatic hydrocarbon group is a monovalent saturated aliphatic hydrocarbon group, an alkyl group, a cycloalkyl group or a monovalent saturated aliphatic hydrocarbon group having a cyclic moiety (such as a cycloalkyl group, a cycloalkylene group or a bicycloalkyl group, a group having an aliphatic spiro structure, or a group having such a group as a partial structure) may, for example, be mentioned, and an alkyl group is preferred. As the monovalent aromatic hydrocarbon group, a phenyl group, an aryl group or such a group having a substituent, is preferred.

As the halogen atom in the present specification, a fluorine atom, a chlorine atom, a bromine atom or an iodine atom may be mentioned, and a fluorine atom, a chlorine atom or a bromine atom is preferred.

Further, in the present specification, "halogeno" means that at least one hydrogen atom present in a group is substituted by at least one halogen atom selected from a fluorine atom, a chlorine atom, a bromine atom and an iodine atom. In the group of a halogeno group, a hydrogen atom may or may not be present.

The "partially halogeno" means that a hydrogen atom which is not substituted by a halogen atom is present in the group of a halogeno group. The "perhalogeno" means that no hydrogen atom is present in the group of a halogeno group.

In this specification, the halogeno monovalent hydrocarbon group may be a group having at least one hydrogen atom in the above-mentioned monovalent hydrocarbon group substituted by a halogen atom. As such a halogeno monovalent hydrocarbon group, a halogeno alkyl group is preferred. As the halogen atom in the halogeno alkyl group, a fluorine atom, a chlorine atom or a bromine atom is preferred. Further, as a partially halogeno monovalent hydrocarbon group, a partially halogeno alkyl group is preferred. As the perhalogeno monovalent hydrocarbon group, a perhalogeno alkyl group is preferred. The halogen atoms in a perhalogeno alkyl group are preferably composed of fluorine atoms only or fluorine atoms and halogen atoms other than fluorine atoms. As specific examples of these groups, groups disclosed in the following examples of compounds may be mentioned.

In the present specification, the hetero atom-containing monovalent saturated hydrocarbon group may be a group containing in the above-mentioned monovalent saturated hydrocarbon a hetero atom which undergoes no change by the fluorination reaction or a hetero atom group which undergoes no change by the fluorination reaction. Particularly preferred is a group containing in a monovalent saturated hydrocarbon group a bivalent hetero atom or a bivalent hetero atom group which undergoes no change by the fluorination reaction.

The bivalent hetero atom which undergoes no change by the fluorination reaction is preferably an etheric oxygen atom, and the bivalent hetero atom group which undergoes no change by the fluorination reaction may, for example, be —C(=O)— or —SO$_2$—.

As the hetero atom-containing monovalent saturated hydrocarbon group, an alkyl group containing an etheric oxygen atom, or a monovalent aliphatic hydrocarbon group having a cyclic portion having an etheric oxygen atom inserted between carbon-carbon atoms, is preferred. Particularly preferred is an alkoxyalkyl group.

Further, the halogeno (hetero atom-containing monovalent saturated hydrocarbon) group may be a group having at least one hydrogen atom in the above-mentioned hetero atom-containing monovalent saturated hydrocarbon group substituted by a halogen atom, and a halogeno(alkoxyalkyl) group is preferred.

In the compound (I), $R^A$ is a monovalent saturated hydrocarbon group, a halogeno monovalent saturated hydrocarbon group, a hetero atom-containing monovalent saturated hydrocarbon group, a halogeno (hetero atom-containing monovalent saturated hydrocarbon) group or a monovalent organic group ($R^H$) which can be converted to $R^{HF}$ by a liquid-phase fluorination reaction.

And, $R^{HF}$ is a group having at least one hydrogen atom in a group selected from a monovalent saturated hydrocarbon group, a partially halogeno monovalent saturated hydrocarbon group, a hetero atom-containing monovalent saturated hydrocarbon group and a partially halogeno (hetero atom-containing monovalent hydrocarbon) group, substituted by a fluorine atom.

When $R^A$ is a monovalent organic group ($R^H$), a specific example of such a group is a group ($R^{H1}$) having a fluorine atom in the desired $R^{HF}$ substituted by a monovalent hetero atom group which can be converted to a fluorine atom by a fluorination reaction, or a group ($R^{H2}$) having at least one carbon-carbon single bond in the desired $R^{HF}$ substituted by a carbon-carbon double bond or a carbon-carbon triple bond. Further, it is preferred that a hydrogen atom or a fluorine atom is bonded to the carbon atom which forms the carbon-carbon double bond or the carbon-carbon triple bond in $R^{H2}$.

Here, the monovalent hetero atom group which can be converted to a fluorine atom by a fluorination reaction may be a carboxyl group. Further, the group ($R^{H2}$) may, for example, be a cyclohexenyl group, a phenyl group, an alkenyl group or an alkynyl group. By a fluorination reaction in a liquid phase, such $R^{H2}$ becomes a carbon-carbon single bond by an addition of fluorine atoms to the carbon atoms forming an unsaturated bond. For example, by the fluorination reaction, the phenyl group becomes a perfluorocyclohexyl group.

Explanation about Compound (I)

In the compound (I), $E^1$ is a reactive group which is capable of forming a bivalent connecting group (E) by a reaction with $E^2$. Such a bivalent connecting group (E) may be a group which changes or does not change by such a reaction.

As the bivalent connecting group (E), an ester bond-containing group such as —CH$_2$OCO— or —CH$_2$OSO$_2$— (provided that the orientation of these groups is not limited). Particularly preferred is —CH$_2$OCO— from the viewpoint of usefulness of the resulting compound. With respect to $E^1$ and $E^2$ in a case where E is an ester bond-containing group, one of them may be —CH$_2$OH, and the other may be —COX (where X is a halogen atom) or —SO$_2$X. Now, a detailed description will be made with reference to a case where the bivalent connecting group (E) is —CH$_2$OCO—.

In the present invention, it is possible to employ various compounds differing in the structure of $R^A$, as the compound (I). Namely, by carrying out the reaction of the present invention by using a compound (I) having a group ($R^A$) corresponding to $R^{AF}$ in the desired compound (V), it is possible to produce a compound (V) which used to be difficult to obtain by a conventional method. Likewise, various compounds differing in the structure of RB can be employed as the compound (II). As an example of the compound (V) which used to be difficult to obtain by a conventional method, a compound wherein the structure of $R^{AF}$ is complex, or a fluorinated product of a low molecular weight whereby various types of by-products tend to form by the fluorination reaction, may be mentioned. As an example of the latter, a fluorinated product of one wherein the molecular weight of the compound (I) is less than 200, preferably one wherein the molecular weight is from 50 to 200, may be mentioned.

The compound (I) is preferably a compound (Ia) wherein $E^1$ is —CH$_2$OH, particularly preferably a compound (Ia-1) wherein $R^A$ is $R^{AH}$, especially preferably a compound (Ia-2) wherein $R^A$ is $R^1$:

$R^A$CH$_2$OH  (Ia)

$R^{AH}$CH$_2$OH  (Ia-1)

$R^1$CH$_2$OH  (Ia-2)

Here, $R^A$ has the same meaning as the meaning in the compound (I). $R^{AH}$ is a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group. $R^1$ is an alkyl group, an alkoxyalkyl group, a halogenoalkyl group or a halogeno (alkoxyalkyl) group.

When $R^1$ is an alkyl group, it is preferably a $C_{1-20}$ alkyl group, particularly preferably a $C_{1-10}$ alkyl group. The alkyl group may be of a straight chain structure, a branched structure, a cyclic structure or a partially cyclic structure. The alkyl group of a straight chain structure may, for example, be a methyl group, an ethyl group, a propyl group or a butyl group. The alkyl group of a branched structure may, for example, be an isopropyl group, an isobutyl group, a sec-butyl group or a tert-butyl group.

When $R^1$ is an alkoxyalkyl group, it is preferably a group having at least one hydrogen atom present in the above-mentioned alkyl group substituted by an alkoxy group. The carbon number of such an alkoxy group is preferably from 1 to 8. Such an alkoxyalkyl group may, for example, be an ethoxymethyl group, a 1-propoxyethyl group or a 2-propoxyethyl group.

When $R^1$ is a halogenoalkyl group, halogen atoms may be of one type or two or more types, and chlorine atoms, bromine atoms, or chorine atoms and bromine atoms, are preferred. As a specific example of such a group, a chloromethyl group, a bromomethyl group, a 2,3-dichloropropyl group or a 3,4-dichlorobutyl group may be mentioned.

When $R^1$ is a halogeno(alkoxyalkyl) group, halogen atoms may be of one type or two or more types, and chlorine atoms, bromine atoms, or chlorine atoms and bromine atoms, are preferred. As a specific example of such a group, a 1-(3,4-dichlorobutoxy)ethyl group or a 1-(2-bromoethoxy) ethyl group may be mentioned.

Further, the compound (Ia-2) is preferably one wherein $R^1$ is $R^4(R^5O)CH$— (wherein each of $R^4$ and $R^5$ which are independent of each other, is an alkyl group or a halogenoalkyl group), a 2,3-dichloropropyl group or an ethyl group, from the viewpoint of usefulness of the product. Namely, the compound (Ia-2) is preferably a compound (Ia-3), 3,4-dichloro-1-butanol or 1-propanol.

$$R^4(R^5O)CHCH_2OH \qquad (Ia\text{-}3)$$

The compound (Ia-3) is preferably 2-propoxy-1-propanol [$(CH_3)(CH_3CH_2CH_2O)CHCH_2OH$] where $R^4$ is a methyl group, and $R^5$ is a n-propyl group.

The following compounds may be mentioned as specific examples of the compound (I). In the following, Cy is a cyclohexyl group, and Ph is a phenyl group.

$CH_3(CH_3CH_2CH_2O)CHCH_2OH$,
$CH_3(CH_2ClCHClCH_2CH_2O)CHCH_2OH$,
$CH_3(BrCH_2CH_2O)CHCH_2OH$,
$CH_3[CH_2ClCHClCH_2CH(CH_3)O]CHCH_2OH$,
$CH_3CH_2CH_2OH$,
$CH_2\!\!=\!\!CHCH_2OH$,
$CH_2ClCHClCH_2OH$,
$CH_2ClCH_2OH$,
$CH_2BrCH_2OH$,
$CyCH_2OCH(CH_3)CH_2OH$,
$PhCH_2OCH(CH_3)CH_2OH$,
$CH_3(CH_2)_9OCH(CH_3)CH_2OH$,
$PhCH_2O(CH_2)_2CH_2OH$,
$CH_2\!\!=\!\!CHCH_2O(CH_2)_2CH_2OH$,
$CH_3CH_2CH_2OCH_2CH(CH_3)OH$,
$CF_2ClCFClCH_2CH_2OH$,

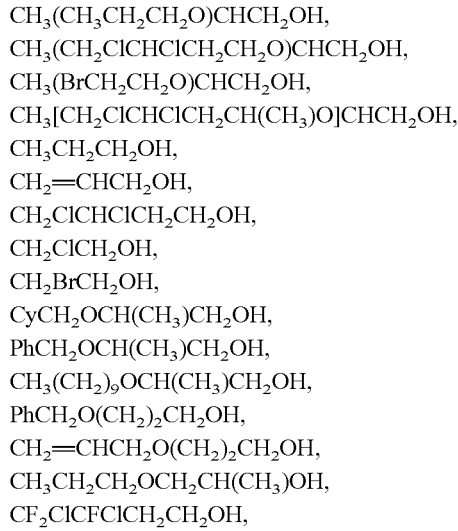

The compound (Ia) is a compound which is readily available or which can readily be synthesized by a known method. For example, 3,4-dichloro-1-butanol can easily be synthesized by a known method disclosed in e.g. U.S. Pat. No. 4,261,901. Further, 2-alkoxyalcohols can be easily synthesized by known methods disclosed, for example, in J. Am. Chem. Soc., 49, 1080 (1927), Bull. Soc. Chim. Fr., 1813(1960), Can. J. Chem., 43, 1030(1965), Synthesis, 280(1981). 3-Alkoxyalcohols can easily be synthesized by known methods disclosed, for example, in Tetrahedron Lett., 36, 9161(1995), J. Org. Chem., 62, 7439(1997). Alcohols having a dioxolane skeleton can easily be synthesized by known methods disclosed, for example, in Bull. Chem. Soc. Jpn., 70, 2561(1997).

Explanation about the Compound (II)

The compound (I) is reacted with the compound (II). In the compound (II), $R^B$ is a monovalent saturated hydrocarbon group, a halogeno monovalent saturated hydrocarbon group, a hetero atom-containing monovalent saturated hydrocarbon group, a halogeno (hetero atom-containing monovalent saturated hydrocarbon) group, or a monovalent organic group ($R^H$) which can be converted to $R^{HF}$ by a fluorination reaction in a liquid phase, and embodiments of these groups are the same as $R^A$. With respect to $R^B$, its structure is preferably adjusted in relation with the structure of $R^A$, so that the resulting compound (III) will be readily soluble in a liquid phase to be used at the time of fluorination.

Further, in the present invention, it is preferred that one or each of $R^A$ and $R^B$ is a monovalent organic group containing fluorine atoms. Further, the fluorine content in the compound (III) (the proportion of fluorine atoms in the molecule) is preferably suitably changed depending upon the type of the liquid phase to be used for the fluorination reaction. Usually, the fluorine content is preferably at least 10 mass %, particularly preferably from 10 to 86 mass %, especially preferably from 10 to 76 mass %, and further preferably from 30 to 76 mass %. It is preferred to select $R^A$ and $R^B$ so that the fluorine content will be within such a range.

$R^A$ may be a group which contains or does not contain fluorine atoms. Whereas, $R^B$ is preferably a perhalogeno group, particularly preferably a perfluoro group, since the after-mentioned continuous process can easily be carried out.

The compound (II) may be a commercial product or the compound (VI) formed by the after-described method of the present invention.

As described above, $E^2$ in the compound (II) is preferably —COX or —SO$_2$X (wherein X is a halogen atom, preferably a chlorine atom or a fluorine atom, and when a continuous process is carried out, X is preferably a fluorine atom), particularly preferably —COX.

Namely, the compound (II) is preferably a compound (IIb) wherein $E^2$ is —COF, particularly preferably a compound (IIb-1) wherein $R^B$ is $R^{BF1}$, especially preferably a compound (IIb-2) wherein $R^B$ is $R^2$.

$$FCOR^B \qquad (IIb)$$

$$FCOR^{BF1} \qquad (IIb-1)$$

$$FCOR^2 \qquad (IIb-2)$$

Here, $R^B$ has the same meaning as the meaning in the compound (II). $R^{BF1}$ is a perhalogeno monovalent saturated hydrocarbon group or a perhalogeno (hetero atom-containing monovalent saturated hydrocarbon) group. $R^2$ is a perhalogenoalkyl group or a perhalogeno(alkoxyalkyl) group.

$R^{BF1}$ is preferably $R^{BF10}$ (wherein $R^{BF10}$ is a perfluoro monovalent saturated hydrocarbon group, a perfluoro (partially chlorinated monovalent saturated hydrocarbon) group, a perfluoro (hetero atom-containing monovalent saturated hydrocarbon) group or a perfluoro (partially chlorinated hetero atom-containing monovalent saturated hydrocarbon) group).

The halogen atom in $R^2$ is preferably a fluorine atom, a chlorine atom or a bromine atom. Further, halogen atoms in $R^2$ may be of one type or two or more types, and particularly preferred is a case where all of the halogen atoms in $R^2$ are fluorine atoms, or 1 or 2 halogen atoms in $R^2$ are chlorine atoms or bromine atoms and all of other halogen atoms are fluorine atoms. $R^2$ is preferably a perfluoroalkyl group, a perfluoro (partially chlorinated alkyl) group, a perfluoro (alkoxyalkyl) group or a perfluoro (partially chlorinated alkoxyalkyl) group.

When $R^2$ is a perhalogenoalkyl group, the carbon number is preferably from 1 to 20, particularly preferably from 1 to 10. Such a group may be of a straight chain structure or a branched structure. When the perhalogenoalkyl group is of a straight chain structure, it may, for example, be —$CF_3$, —$CF_2CF_3$, —$CF_2CF_2CF_3$, —$CF_2CF_2CF_2CF_3$, —$CClF_2$, —$CBrF_2$ or —$CF_2CFClCF_2Cl$. When the perhalogeno alkyl group is of a branched structure, it may, for example, be —$CF(CF_3)_2$, —$CF_2CF(CF_3)_2$, —$CF(CF_3)CF_2CF_3$ or —$C(CF_3)_3$.

When $R^2$ is a perhalogeno(alkoxyalkyl) group, the structure of the alkoxyalkyl group moiety is preferably a structure having one hydrogen atom present in a $C_{1-20}$ (preferably $C_{1-10}$) alkyl group substituted by a $C_{1-8}$ alkoxy group.

As an example of a case where $R^2$ is a perhalogeno (alkoxyalkyl) group, —$CF(OCF_2CF_2CF_3)CF_3$, —$CF(OCF_2CF_2CFClCF_2Cl)CF_3$ or —$CF(OCF_2CF_2Br)CF_3$ may, for example, be mentioned.

From the usefulness of the product, the compound (IIb-2) is preferably the following compound (IIb-3) (wherein each of $R^8$ and $R^9$ which are independent of each other, is a perhalogenoalkyl group), a compound (IIb-2) wherein $R^2$ is —$CF_2CFClCF_2Cl$, or $CF_3CF_2COF$.

$$FCOCFR^8(OR^9) \qquad (IIb-3)$$

The following compounds may be mentioned as specific examples of the compound (II):
$CF_3CF_2COF$,
$CF_2ClCFClCF_2COF$,
$CF_2ClCF_2CFClCOF$,
$CF_3(CF_3CF_2CF_2O)CFCOF$,
$CF_3(CF_2ClCFClCF_2CF_2O)CFCOF$,
$CClF_2COF$,
$CBrF_2COF$,
$CF_3(CF_2BrCF_2O)CFCOF$,
$CF_3[CF_2ClCFClCF_2CF(CF_3)O]CFCOF$,
$CF_3CF_2CF_2OCF(CF_3)CF_2OCF(CF_3)COF$,
$CF_3(CH_3CH_2CH_2O)CFCOF$,
$CH_2ClCHClCH_2COCl$.

As the compound (II), $CF_3(CF_3CF_2CF_2O)CFCOF$ is particularly preferred. This compound can be readily available as an intermediate for a perfluoro(alkyl vinyl ether).

The reaction of the compound (I) with the compound (II) can be carried out by applying known reaction methods and conditions depending upon the structures of $E^1$ and $E^2$ and their combination. For example, the reaction of the compound (Ia) wherein $E^1$ is —$CH_2OH$ with a compound (IIb) wherein $E^2$ is —COX, can be carried out under known reaction conditions. Such reaction may be carried out in the presence of a solvent (hereinafter referred to as solvent 1), but it is preferred to carry out the reaction in the absence of solvent 1, from the viewpoint of the volume efficiency. In a case where solvent 1 is used, dichloromethane, chloroform, triethylamine or a solvent mixture of triethylamine with tetrahydrofuran, is preferred. The amount of solvent 1 is preferably from 50 to 500 mass %, based on the total amount of the compound (Ia) and the compound (IIb).

In the reaction of the compound (Ia) with the compound (IIb), an acid represented by HX will be formed. When a compound wherein X is a fluorine atom is used as the compound (IIb), HF will be formed, and as a capturing agent for HF, an alkali metal fluoride (preferably NaF or KF) or a trialkylamine may be present in the reaction system. It is preferred to use a capturing agent for HF, when the compound (Ia) or the compound (IIb) is a compound which is unstable against an acid. Further, when a capturing agent for HF is not used, it is preferred to discharge HF out of the reaction system as accompanied in a nitrogen stream. When an alkali metal fluoride is employed, its amount is preferably from 1 to 10 mol times, based on the compound (IIb).

The temperature for the reaction of the compound (Ia) with the compound (IIb) is usually preferably at least −50° C., and preferably at most +100° C. or at most the boiling point temperature of the solvent. Further, the reaction time of such a reaction may be suitably changed depending upon the supply rates of the starting materials and the amounts of the compounds to be used for the reaction. The reaction pressure (gauge pressure, the same applies hereinafter) is preferably from atmospheric pressure to 2 MPa.

Explanation about the Compound (III)

By the reaction of the compound (I) with the compound (II), a compound (III) will be formed. In the compound (III), $R^A$ is the same group as $R^A$ in the compound (I), and $R^B$ is the same group as $R^B$ in the compound (II). E is a bivalent connecting group formed by the reaction of $E^1$ with $E^2$, and the above-mentioned groups may be mentioned. The molecular weight of the compound (III) is preferably from 200 to 1000, whereby the fluorination reaction in a liquid phase can be smoothly carried out. If the molecular weight is too small, the compound (III) tends to be readily volatile, and it is likely that a decomposition reaction may take place in a gas phase during the fluorination reaction in a liquid phase. On the other hand, if the molecular weight is too large, purification of the compound (III) tends to be difficult.

Further, the fluorine content in the compound (III) is preferably the above-mentioned amount. The compound (III) is preferably a compound (IIIc) which is formed by the reaction of the compound (Ia) with the compound (IIb), particularly preferably a compound (IIIc-1) which is formed by the reaction of the compound (Ia-1) with the compound (IIb-1), especially preferably a compound (IIIc-2) which is formed by the reaction of a compound (Ia-2) with a compound (IIb-2):

R<sup>A</sup>CH$_2$OCOR<sup>B</sup>　　　(IIIc)

R<sup>AH</sup>CH$_2$OCOR<sup>BF1</sup>　　　(IIIc-1)

R<sup>1</sup>CH$_2$OCOR<sup>2</sup>　　　(IIIc-2)

wherein R<sup>A</sup>, R<sup>B</sup>, R<sup>AH</sup>, R<sup>BF1</sup>, R<sup>1</sup> and R<sup>2</sup> have the same meanings as described above, and the preferred embodiments are also the same.

The compound (IIIc-2) is preferably a compound (IIIc-20) wherein R<sup>1</sup> is R<sup>4</sup>(R<sup>5</sup>O)CH—, a compound (IIIc-21) wherein R<sup>2</sup> is —CFR<sup>8</sup>(OR<sup>9</sup>), or CF$_3$CF$_2$COOCH$_2$CH$_2$CH$_3$ wherein R<sup>1</sup> is an ethyl group, and R<sup>2</sup> is a pentafluoroethyl group. Further, the compound (IIIc-2) is preferably a compound (IIIc-3) wherein R<sup>1</sup> is R<sup>4</sup>(R<sup>5</sup>O)CH—, and R<sup>2</sup> is —CFR<sup>8</sup>(OR<sup>9</sup>), especially preferably a compound (IIIc-30):

R<sup>4</sup>(R<sup>5</sup>O)CHCH$_2$OCOR<sup>2</sup>　　　(IIIc-20)

R$_1$CH$_2$OCOCFR<sup>8</sup>(OR<sup>9</sup>)　　　(IIIc-21)

R<sup>4</sup>(R<sup>5</sup>O)CHCH$_2$OCOCFR<sup>8</sup>(OR<sup>9</sup>)　　　(IIIc-3)

CH$_3$(CH$_3$CH$_2$CH$_2$O)CHCH$_2$OCOCFR<sup>8</sup>(OR<sup>9</sup>)　　　(IIIc-30)

The following compounds may be mentioned as specific examples of the compound (III):

CF$_3$CF$_2$COOCH$_2$CH$_2$CH$_3$,
CF$_3$CF$_2$COOCH$_2$CH(OCH$_2$CH$_2$CH$_3$)CH$_3$,
CF$_3$CF$_2$COOCH$_2$CH(OCH$_2$CH$_2$CHClCH$_2$Cl)CH$_3$,
CF$_3$CF$_2$COO(CH$_2$)$_4$OCHClCH$_2$C$_1$,
CF$_3$CF$_2$COO(CH$_2$)$_5$OCHClCH$_2$C$_1$,
CF$_3$(CF$_3$CF$_2$CF$_2$O)CFCOO(CH$_2$)$_4$OCHClCH$_2$C$_1$,
CF$_3$(CF$_3$CF$_2$CF$_2$O)CFCOO(CH$_2$)$_5$OCHClCH$_2$C$_1$,
CF$_3$(CF$_2$ClCFClCF$_2$CF$_2$O)CFCOOCH$_2$CH(OCH$_2$CH$_2$CHClCH$_2$Cl)CH$_3$,
CF$_2$ClCFClOCF$_2$CF$_2$CF$_2$COO(CH$_2$)$_4$OCHClCH$_2$Cl,
CClF$_2$COOCH$_2$CH$_2$Cl,
CBrF$_2$COOCH$_2$CH$_2$Br,
CF$_2$BrCF$_2$OCF(CF$_3$)COOCH$_2$CH(OCH$_2$CH$_2$Br)CH$_3$,
CF$_2$ClCFClCF$_2$CF(CF$_3$)OCF(CF$_3$)COOCH$_2$CH[OCH(CH$_3$)CHClCH$_2$Cl]CH$_3$,
CH$_2$ClCHClCH$_2$COOCH$_2$CF$_2$CFClCF$_2$Cl,
CF$_3$(CH$_3$CH$_2$CH$_2$O)CFCOOCH$_2$CF(OCF$_2$CF$_2$CF$_3$)CF$_3$,
CF$_3$(CH$_3$CH$_2$CH$_2$O)CFCOOCH$_2$CF(OCH$_2$CH$_2$CH$_3$)CF$_3$,
CF$_3$(CF$_3$CF$_2$CF$_2$O)CFCOOCH$_2$CH(OCH$_2$CH$_2$CH$_3$)CH$_3$,
CF$_3$(CF$_3$CF$_2$CF$_2$O)CFCOOCH$_2$CH(OCH$_2$CH$_2$CHClCH$_2$Cl)CH$_3$,
CF$_3$(CF$_3$CF$_2$CF$_2$O)CFCOOCH$_2$CH(OCH$_2$Cy)CH$_3$,
CF$_3$(CF$_3$CF$_2$CF$_2$O)CFCOOCH$_2$CH(OCH$_2$Ph)CH$_3$,
CF$_3$(CF$_3$CF$_2$CF$_2$O)CFCOOCH$_2$CH(O(CH$_2$)$_9$CH$_3$)CH$_3$,
CF$_3$(CF$_3$CF$_2$CF$_2$O)CFCOO(CH$_2$)$_3$OCH$_2$ Ph,
CF$_3$(CF$_3$CF$_2$CF$_2$O)CFCOO(CH$_2$)$_3$OCH$_2$CH=CH$_2$.
CF$_3$CF$_2$COOCH$_2$CH$_2$CHClCH$_2$Cl,
CF$_2$ClCFClCF$_2$COOCH$_2$CH$_2$CHClCH$_2$Cl,
CF$_2$ClCF$_2$CFClCOOCH$_2$CH$_2$CHClCH$_2$Cl,

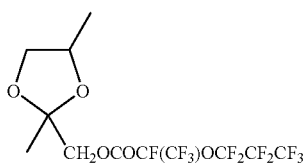

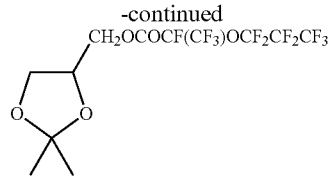

The above-mentioned novel compound (III) is useful as an intermediate for a fluorinated resin material, and can be led to a fluorinated resin material by the after-described reaction. Especially in the novel compound (III), a compound having —CHClCH$_2$Cl at its molecular terminals can be led to a fluorinated resin material having two polymerizable unsaturated groups.

A crude product containing the compound (III) formed by the reaction of the compound (I) with the compound (II), may be purified depending upon the particular purpose or may be used for the next reaction as it is. With a view to carrying out the fluorination reaction of the next step safely, it is preferred that the compound (III) in the crude product is separated and purified.

The purification method of the crude product may, for example, be a method of distilling the crude product directly, a method of treating the crude product with a dilute alkali water, followed by liquid separation, a method of extracting the crude product with a suitable organic solvent, followed by distillation, or silica gel column chromatography.

Explanation about the Compound (IVd)

Then, in the present invention, the compound (III) is fluorinated in a liquid phase to obtain a compound (IV). The fluorination in a liquid phase is preferably carried out by a method of fluorinating the compound (IIIc) in a solvent with fluorine gas (fluorination method-1) or by electrochemical fluorination (fluorination method-2), particularly preferably fluorination method-1.

When fluorination is carried out by fluorination method-2, it is preferred that the compound (III) is dissolved in anhydrous hydrofluoric acid to obtain a solution, and this solution is electrolyzed in an electrolytic cell to fluorinate the compound (III) to form a compound (IV).

When fluorination is carried out in fluorination method-1, the compound (III) and fluorine gas are reacted in a solvent (hereinafter referred to as solvent-2) to form a compound (IV). The fluorine gas may be used as it is, or fluorine gas diluted with an inert gas may be employed. As the inert gas, nitrogen gas or helium gas is preferred, and nitrogen gas is particularly preferred from an economical reason. The amount of fluorine gas in the nitrogen gas is not particularly limited, and at least 10% is preferred from the viewpoint of the efficiency, and at least 20% is particularly preferred.

Solvent-2 to be used for fluorination method-1 is preferably a solvent which contains no C—H bond and which necessarily contains a C—F bond. Further, a perfluoroalkane or an organic solvent obtained by perfluorinating a known organic solvent having at least one atom selected from a chlorine atom, a nitrogen atom and an oxygen atom in its structure, is preferred. Further, as solvent-2, it is preferred to employ a solvent which provides a high solubility to the compound (III), and it is particularly preferred to employ a solvent which is capable of dissolving at least 1 mass % of the compound (III), particularly a solvent which is capable of dissolving at least 5 mass %.

Examples of solvent-2 may be a compound (IIb-2), an after-described compound (IVd-2), perfluoroalkanes (such as FC-72), perfluoroethers (such as FC-75 and FC-77), perfluoropolyethers (tradenames: KRYTOX, FOMBLIN, GALDEN and Demnum), chlorofluorocarbons (tradename: Flon Lube), chlorofluoropolyesters, perfluoroalkylamines [such as perfluorotrialkylamine], and an inert fluid (tradename: Fluorinert). Among them, a perfluorotrialkylamine, the compound (V) or the compound (VI) (preferably the compound (IIb-2), the compound (IV) (preferably the compound (IVd-2)) is preferred. Particularly when the compound (IV), the compound (V) or the compound (VI) is employed, there will be a merit that workup after the reaction will be easy. The amount of solvent-2 is preferably at least five times by mass, particularly from 10 to 100 times by mass, relative to the compound (III).

The reaction type of the fluorination reaction of fluorination method-1 is preferably a batch system or a continuous system. Especially from the viewpoint of the reaction yield and selectivity, a continuous system (2) which will be described hereinafter, is preferred. Further, fluorine gas may be one diluted with an inert gas such as nitrogen gas either when the reaction is carried out by a batch system or when it is carried out by a continuous system.

Continuous system (1) Into a reactor, the compound (III) and solvent-2 are charged, and stirring is initiated. A method of reacting at a predetermined reaction temperature and reaction pressure while supplying fluorine gas continuously Continuous system (2) Into a reactor, solvent-2 is charged, and stirring is initiated. A method of supplying the compound (III), solvent-2 and fluorine gas under a predetermined reaction temperature and reaction pressure in a predetermined molar ratio continuously and simultaneously. In the continuous system (2), when the compound (III) is supplied, it is preferred to supply the compound (III) as diluted with solvent-2, to improve the selectivity and to suppress the amount of by-products. Further, in the continuous system (2), when the compound (III) is diluted with the solvent, it is preferred to adjust the amount of solvent-2 to at least five times by mass, particularly preferably at least ten times by mass, relative to the compound (III).

With respect to the amount of fluorine to be used for the fluorination reaction, when the reaction is carried out by a batch system, it is preferred to charge fluorine gas so that the amount of fluorine atoms is always excess equivalent, relative to hydrogen atoms in the compound (III), and it is particularly preferred that fluorine gas is used so that it becomes at least 1.5 times by equivalent, from the viewpoint of selectivity. Further, when the reaction is carried out by a continuous process, it is preferred to continuously supply fluorine gas so that the amount of fluorine atoms will be excess equivalent, relative to hydrogen atoms in the compound (III), and it is particularly preferred to continuously supply fluorine gas so that it becomes at least 1.5 times by equivalent, relative to the compound (III), from the viewpoint of selectivity.

The reaction temperature for the fluorination reaction by fluorination method-1 may be varied depending upon the structure of the bivalent connecting group (E), but it is usually preferably at least −60° C. and at most the boiling point of the compound (III), and from the viewpoint of the reaction yield, the selectivity and efficiency for industrial operation, it is particularly preferably from −50° C. to +100° C., especially preferably from −20° C. to +50° C. The reaction pressure of the fluorination reaction is not particularly limited, and it is particularly preferably from atmospheric pressure to 2 MPa from the viewpoint of the reaction yield, the selectivity and efficiency for industrial operation.

Further, in order to let fluorination method-1 proceed efficiently, it is preferred to add a C—H bond-containing compound to the reaction system or to carry out in the presence of ultraviolet light. For example, in a batch system reaction, it is preferred to add a C—H bond-containing compound to the reaction system or to carry out in the presence of ultraviolet light at a later stage of the fluorination reaction. In a continuous system reaction, it is preferred to add a C—H bond-containing compound, or to carry out in the presence of ultraviolet light, whereby the compound (III) present in the reaction system can efficiently be fluorinated, and the reaction rate can remarkably be improved. The time for ultraviolet irradiation is preferably from 0.1 to 3 hours.

The C—H bond-containing compound is an organic compound other than the compound (III), and an aromatic hydrocarbon is particularly preferred. Especially preferred is, for example, benzene or toluene. The amount of such a C—H bond-containing compound is preferably from 0.1 to 10 mol %, particularly preferably from 0.1 to 5 mol %, relative to hydrogen atoms in the compound (III).

It is preferred to add the C—H bond-containing compound in such a state where fluorine gas is present in the reaction system. Further, when the C—H bond-containing compound is added, it is preferred to pressurize the reaction system. The pressure during the pressurizing is preferably from 0.01 to 5 MPa.

In the fluorination reaction of the compound (III), a compound (IV) will be formed. In the compound (IV), $R^{AF}$ is a group corresponding to $R^A$, and $R^{BF}$ is a group corresponding to $R^B$. In a case where each of $R^A$ and $R^B$ is a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group, each of $R^{AF}$ and $R^{BF}$ is the same group as $R^A$ and $R^B$, respectively, or a group having at least one hydrogen atom present in the group of $R^A$ or $R^B$ substituted by a fluorine atom. $R^{AF}$ and $R^{BF}$ are preferably groups which are substituted by fluorine, and in such groups, non-substituted hydrogen atoms may be present. The amounts of hydrogen atoms in such groups are preferably suitably changed depending upon the particular purpose.

Further, when a compound (III) wherein hydrogen atoms are present in $R^A$ and $R^B$, is fluorinated, $R^{AF}$ and $R^{BF}$ in the compound (IV) to be formed, may be groups wherein hydrogen atoms may or may not be present, preferably groups wherein no hydrogen atoms are present, particularly preferably groups wherein all of hydrogen atoms in $R^A$ and $R^B$ are substituted by fluorine atoms.

Further, in a case where even if hydrogen atoms are present in $R^A$ and $R^B$, such hydrogen atoms are not susceptible to fluorination, or in a case where a compound (III) wherein $R^A$ and $R^B$ are perhalogeno groups, is employed, $R^{AF}$ and $R^{BF}$ in the compound (IV) are the same groups as $R^A$ and $R^B$, respectively. In a case where $R^A$ and $R^B$ are monovalent organic groups ($R^H$), $R^{AF}$ and $R^{BF}$ are $R^{HF}$ corresponding to such $R^H$, respectively.

In the fluorination reaction in a liquid phase, it is difficult to adjust the position for introduction of a fluorine atom, and accordingly, $R^{AF}$ and $R^{BF}$ in the compound (IV) are preferably groups which contain no hydrogen atoms. Namely, when a compound (III) wherein each of $R^A$ and $R^B$ is a group containing hydrogen atoms, is employed, it is preferred to obtain a compound (IV) having $R^{AF}$ and $R^{BF}$ wherein all of such hydrogen atoms are substituted by fluorine atoms.

Each of $R^{AF}$ and $R^{BF}$ is preferably a perfluoro monovalent saturated hydrocarbon group, a perfluoro (partially halogeno monovalent saturated hydrocarbon) group, a perfluoro (hetero atom-containing monovalent saturated hydrocarbon) group, or a perfluoro [partially halogeno (hetero atom-containing monovalent saturated hydrocarbon)] group.

$E^F$ is the same group as E, or a group having E fluorinated. An example of the latter group may be a group having at least one hydrogen atom present in E fluorinated, or in a case where a —CH═CH— moiety is present in E, a group having fluorine atoms added to such moiety to form —CF$_2$CF$_2$—. Further, the compound (IV) is not of the same structure as the compound (III), and at least one of $R^{AF}$, $R^{BF}$ and $E^F$ is of a structure different from the corresponding $R^A$, $R^B$ and E, respectively. Namely, at least one of $R^A$, $R^B$ and E is a group modified by the fluorination reaction.

The compound (IV) is preferably a compound (IVd) which is formed by fluorination of a compound (III) wherein E is —CH$_2$OCO—, particularly preferably a compound (IVd-1) which is formed by completely fluorinating the compound (IIIc-1), especially preferably a compound (IVd-2) which is formed by completely fluorinating the compound (IIIc-2):

$R^{AF}CF_2OCOR^{BF}$ (IVd)

$R^{AF1}CF_2OCOR^{BF1}$ (IVd-1)

$R^3CF_2OCOR^2$ (IVd-2)

wherein $R^{AF}$ and $R^{BF}$: the same meanings as the meanings in the compound (IV);

$R^{AF1}$: $R^{AF1}$ is a group corresponding to $R^{AH}$, and when $R^{AH}$ is a group containing hydrogen atoms, a group having all of hydrogen atoms in such a group substituted by fluorine atoms, and when $R^{AH}$ is a group containing no hydrogen atom, the same group as $R^{AH}$;

$R^{BF1}$: A perhalogeno monovalent saturated hydrocarbon group or a perhalogeno (hetero atom-containing monovalent saturated hydrocarbon) group;

$R^3$: A group corresponding to $R^1$, and when $R^1$ is a group containing no hydrogen atom, the same group as $R^1$, and when $R^1$ is a group containing hydrogen atoms, a group having all of hydrogen atoms in such a group substituted by fluorine atoms;

$R^2$: The same group as $R^2$ in (IIIc-2).

Further, from the viewpoint of usefulness, the compound (IVd-2) is preferably a compound (IVd-20) where $R^3$ is $R^6(R^7O)CF$—, a compound (IVd-21) where $R^2$ is —CFR$^8$(OR$^9$), or perfluoro(propyl propionate) where $R^2$ and $R^3$ are perfluoroethyl groups:

$R^6(R^7O)CFCF_2OCOR^2$ (IVd-20)

$R^3CF_2OCOCFR^8(OR^9)$ (IVd-21)

wherein $R^2$, $R^3$: The same meanings as described above;

$R^6$: A group corresponding to $R^4$, and when $R^4$ is a group containing no hydrogen atom, the same group as $R^4$, and when $R^4$ is a group containing hydrogen atoms, a group having all of hydrogen atoms in such a group substituted by fluorine atoms;

$F^7$: A group corresponding to $R^5$, and when $R^5$ is a group containing no hydrogen atom, the same group as $R^5$, and when $R^7$ is a group containing hydrogen atoms, a group having all of hydrogen atoms in such a group substituted by fluorine atoms;

$R^8$, $R^9$: The same meanings as described above.

Further, the compound (IVd-2) is preferably a compound (IVd-3) where $R^3$ is $R^6(R^7O)CF$—, and $R^2$ is —CFR$^8$(OR$^9$). Such compound (IVd-3) can be produced by the following production route. Namely, it is obtainable by reacting the compound (Ia-3) with the compound (IIb-3) to form a compound (IIIc-3) and fluorinating the compound (IIIc-3) in a liquid phase (preferably by reacting with fluorine gas in a solvent). The symbols in the following formulae have the same meanings as described above.

$R^4(R^5O)CHCH_2OH(Ia-3)+FCOCFR^8(OR^9)(IIb-3)$
→$R^4(R^5O)CHCH_2OCOCFR^8(OR^9)(IIIc-3)$→$R^6(R^7O)CFCF_2OCOCFR^8(OR^9)(IVd-3)$

The following compounds may be mentioned as specific examples of the compound (IV)

CF$_3$CF$_2$COOCF$_2$CF(OCF$_2$CF$_2$CF$_3$)CF$_3$,
CF$_3$CF$_2$COOCF$_2$CF(OCF$_2$CF$_2$CFClCF$_2$Cl)CF$_3$,
CF$_3$(CF$_2$ClCFClCF$_2$CF$_2$O)CFCOOCF$_2$CF
(OCF$_2$CF$_2$CFClCF$_2$Cl)CF$_3$,
CClF$_2$COOCF$_2$CF$_2$Cl,
CBrF$_2$COOCF$_2$CF$_2$Br,
CF$_3$(CF$_2$BrCF$_2$O)CFCOOCF$_2$CF(OCF$_2$CF$_2$Br)CF$_3$,
CF$_3$[CF$_2$ClCFClCF$_2$CF(CF$_3$)O] CFCOOCF$_2$CF[OCF
(CF$_3$)CF$_2$CFClCF$_2$Cl]CF$_3$,
CF$_3$CF$_2$COOCF$_2$CF(OCHFCF$_2$CFClCF$_2$Cl)CF$_3$,
CF$_3$(CF$_3$CF$_2$CF$_2$O)CFCOOCF$_2$CF
(OCHFCF$_2$CFClCF$_2$Cl)CF$_3$,
CF$_3$(CF$_3$CF$_2$CF$_2$O)CFCOOCF$_2$CF(OCF$_2$CF$_2$CF$_3$)CF$_3$,
CF$_3$CF$_2$COOCF$_2$CF$_2$CF$_3$,
CF$_3$CF$_2$COOCF$_2$CF$_2$CFClCF$_2$Cl,
CF$_2$ClCFClCF$_2$COOCF$_2$CF$_2$CFClCF$_2$Cl,
CF$_2$ClCF$_2$CFClCOOCF$_2$CF$_2$CFClCF$_2$Cl,
CF$_3$(CF$_3$CF$_2$CF$_2$O)CFCOOCF$_2$CF
(OCF$_2$CF$_2$CFClCF$_2$Cl)CF$_3$,
CF$_3$(CF$_3$CF$_2$CF$_2$O)CFCOOCF$_2$CF(OCF$_2$CY$^F$)CF$_3$,
CF$_3$(CF$_3$CF$_2$CF$_2$O)CFCOOCF$_2$CF(O(CF$_2$)$_9$CF$_3$)CF$_3$,
CF$_3$(CF$_3$CF$_2$CF$_2$O)CFCOO(CF$_2$)$_3$OCF$_2$Cy$^F$,
CF$_3$(CF$_3$CF$_2$CF$_2$O)CFCOO(CF$_2$)$_3$OCF$_2$CF$_2$CF$_3$,

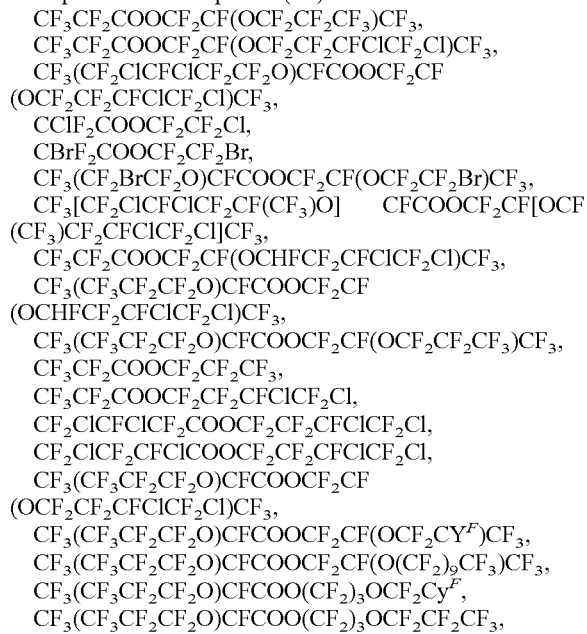

In the liquid-phase fluorination reaction of the compound (III), when a reaction to substitute hydrogen atoms with fluorine atoms takes place, HF will be formed as a by-product. To remove HF formed as a by-product, it is preferred to incorporate an HF scavenger in the reaction system or to contact the outlet gas with an HF scavenger at the gas outlet of the reactor. As such an HF scavenger, the same as described above may be employed, and NaF is preferred.

When the HF scavenger is incorporated in the reaction system, the amount is preferably from 1 to 20 mol times, more preferably from 1 to 5 mol times, relative to the total amount of hydrogen atoms present in the compound (III). In a case where the HF scavenger is disposed at the outlet of the reactor, it is preferred to arrange (1) a condenser (preferably maintained at a temperature of from 10° C. to room temperature, particularly preferably at about 20° C.) (2) a NaF pellet packed layer and (3) a condenser (preferably maintained at a temperature of from −78° C. to +10° C., more preferably from −30° C. to 0° C.) in a series in the order of (1)-(2)-(3). Further, a liquid-returning line may be installed to return the condensed liquid from the condenser of (3) to the reactor.

The crude product containing the compound (IV) obtained by the fluorination reaction may be employed for the next step as it is or may be purified to a high purity. The purification method may, for example, be a method of distilling the crude product as it is under atmospheric pressure or reduced pressure.

Explanation about the Compound (Ve)

In the present invention, the compound (IV) is further converted to a compound (V). Such a conversion reaction is a reaction to dissociate $E^F$ in the compound (IV) into $E^{F1}$ and $E^{F2}$. The method and conditions of the conversion reaction may suitably be changed depending upon the structure of the compound (IV). In a case where the compound (IV) is a compound (IVd), the conversion reaction is a reaction to dissociate —$CF_2OCO$—.

The conversion reaction of the compound (IVd) is preferably carried out by a thermal decomposition reaction or a decomposition reaction which is carried out in the presence of a nucleophile or an electrophile. By such a reaction, a compound (Ve) and the compound (VIf) wherein $E^{F1}$ and $E^{F2}$ are —COF, will be formed.

The thermal decomposition reaction can be carried out by heating the compound (IVd). The reaction type of the thermal decomposition reaction is preferably selected from the boiling point and the stability of the compound (IVd). For example, when a compound (IVd) which is readily vaporized, is to be thermally decomposed, a gas phase thermal decomposition method may be employed in which it is continuously decomposed in a gas phase, and the outlet gas containing the obtained compound (Ve) is condensed and recovered.

The reaction temperature of the gas phase thermal decomposition method is preferably from 50 to 350° C., particularly preferably from 50 to 300° C., especially preferably from 150 to 250° C. Further, an inert gas which is not concerned directly with the reaction, may be present in the reaction system. As such an inert gas, nitrogen or carbon dioxide may, for example, be mentioned. It is preferred to add an inert gas in an amount of from 0.01 to 50 vol % relative to the compound (IVd). If the amount of the inert gas is large, the recovery of the product may sometimes decrease. The method and conditions of the gas phase decomposition method can be applied to any compound contained in the scope of the compound (IVd).

On the other hand, in a case where the compound (IV) is a compound which is hardly vaporized, it is preferred to employ a liquid phase thermal decomposition method wherein it is heated in the state of a liquid in the reactor. The reaction pressure in this case is not limited. In a usual case, the product containing the compound (Ve) is of a lower boiling point, and it is preferred to obtain the product by a method of a reaction distillation type wherein the product is vaporized and continuously withdrawn. Otherwise, it may be a method wherein after completion of the heating, the product is withdrawn all together from the reactor. The reaction temperature for this liquid phase thermal decomposition method is preferably from 50 to 300° C., particularly preferably from 100 to 250° C.

When the thermal decomposition is carried out by the liquid phase thermal decomposition method, the decomposition may be carried out in the absence of a solvent or in the presence of a solvent (hereinafter referred to as solvent-3). Solvent-3 is not particularly limited so long as it is not reactive with the compound (IVd) and it is compatible with the compound (IVd) and is not reactive with the resulting compound (Ve). Further, as solvent-3, it is preferred to select one which is readily separable at the time of purification of the compound (Ve). A specific example of solvent-3 may be an inert solvent such as perfluorotrialkylamine or perfluoronaphthalene, or a chlorofluorocarbon, particularly preferably chlorotrifluoroethylene oligomer having a high boiling point (for example, tradename: Flon Lube). Further, the amount of solvent-3 is preferably from 10 to 1000 mass % relative to the compound (IVd).

Further, in a case where the compound (IVd) is decomposed by reacting it with a nucleophile or an electrophile in a liquid phase, such a reaction may be carried out in the absence of a solvent or in the presence of a solvent (hereinafter referred to as solvent-4). Solvent-4 is preferably the same as solvent-3. The nucleophile is preferably a fluoride anion ($F^-$), particularly preferably a fluoride anion derived from an alkali metal fluoride. The alkali metal fluoride is preferably NaF, $NaHF_2$, KF or CsF. Among them, NaF is particularly preferred from the viewpoint of economical efficiency.

When the nucleophile such as ($F^-$) is employed, $F^-$ is nucleophilically added to a carbonyl group present in the ester bond of the compound (IVd), whereby $R^{AF}CF_2O^-$ will be detached, and an acid fluoride [compound (VIf)] will be formed. From $R^{AF}CF_2O^-$, $F^-$ will further be detached to form an acid fluoride [compound (Ve)]. The detached $F^-$ will react with another molecule of the compound (VId) in the same manner. Accordingly, the nucleophile to be used at the initial stage of the reaction may be in a catalytic amount or may be used excessively. Namely, the amount of the nucleophile such as $F^-$ is preferably from 1 to 500 mol %, particularly preferably from 10 to 100 mol %, especially preferably from 5 to 50 mol %, relative to the compound (IVd). The reaction temperature is preferably from −30° C. to the boiling point of the solvent or the compound (IVd), particularly preferably from −20° C. to 250° C. This method is also preferably carried out by the distillation column type production method.

In the conversion reaction of the compound (IVd), the compound (Ve) and/or the compound (VIf) will be formed; in the conversion reaction of the compound (IVd-1), the compound (Ve-1) and/or the compound (VIf-1) will be formed; in the thermal decomposition of the compound (IVd-2), the compound (Ve-2) and/or the compound (IIb-2) will be formed; and in the thermal decomposition of the compound (IVd-3), the compound (Ve-3) and/or the compound (VIe-3) will be formed.

$$R^{AF}COF \tag{Ve}$$

$$R^{BF}COF \tag{VIf}$$

$$R^{AF1}COF \tag{Ve-1}$$

$$R^{BF1}COF \tag{VIf-1}$$

$$R^3COF \tag{Ve-2}$$

R²COF (IIb-2)

R⁶(R⁷O)CFCOF (Ve-3)

R⁸(R⁹O)CFCOF (VIe-3)

wherein the meanings of $A^F$, $B^F$, $R^2$, $R^3$, $R^6$ to $R^9$ and $R^{BF1}$ are the same as the above meanings, and $R^{AF1}$ is a group corresponding to $R^{AH}$, and each represents a perhalogeno monovalent saturated hydrocarbon group or a perhalogeno (hetero atom-containing monovalent saturated hydrocarbon) group.

The following compounds may be mentioned as specific examples of the compound (Ve):
CF₃CF₂COF,
CF₂ClCFClCF₂COF,
CF₂ClCF₂CFClCOF,
CF₃(CF₃CF₂CF₂O)CFCOF,
CF₃(CF₂ClCFClCF₂CF₂O)CFCOF,
CF₃(CF₂ClCFClCF₂CHFO)CFCOF.
FCOCF(O(CF₂)₉CF₃)CF₃,
FCO(CF₂)₂OCF₂Cy^F, Among the compound (Ve) and/or the compound (VIf) thereby obtainable, a compound having a partial structure of "C¹F—C²—COF" at the molecular terminals, can be led to a fluorine resin material by converting the molecular terminals to "C¹=C²" by a known reaction (Methods of Organic Chemistry, 4, Vol.10b, Part 1, p. 703, etc.). Namely, the novel compound (Ve) and/or the compound (VIf) is a compound useful as a precursor for a fluorinated resin material. Further, the novel compound (IIIc) and compound (IVd) are compounds useful as intermediates for such precursors.

The novel compound presented by the present invention, can be led to a useful fluorinated resin material by a method which will be described below. Namely, a compound (IIb) or a compound (IIIc) wherein $R^B$ and $R^{BF}$ are CF₃(CF₃CF₂CF₂O)CF—, can be led to a compound (IIb-30) which is a precursor for a useful fluorinated resin material (CF₃CF₂CF₂OCF=CF₂) by the following route. For example, the production route wherein $R^B$ and $R^{BF}$ are CF₃(CF₃CF₂CF₂O)CF—, will be represented as follows:

Further, in a case where an unsaturated bond is present in $R^A$ in the compound (IIb) (for example, a phenyl is present in $R^A$), a product (IIb-30) will be obtained by the following reaction:

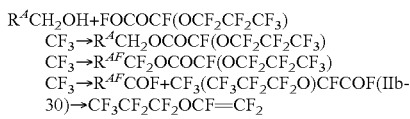

Further, in a case where $R^A$ in the compound (IIb-1) is CH₂ClCHCl—, such a compound can be led to a compound (IIb-21) useful as a perfluoro(butenyl vinyl ether) [CF₂=CFCF₂CF₂OCF=CF₂] material by the following production route:

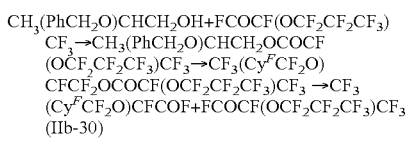

Further, CF₃CF₂COOCF₂CF₂CF₃ can be led to CF₃CF₂COF (IIb-20) useful as a pentafluoropropionyl fluoride material by the method of the present invention. The compound (IIb-20) may be added to the reaction system for the dimerization reaction of hexafluoropropylene oxide, whereby compound (IIb-30) can be produced efficiently (JP-A-11-116529, etc).

Further, in a case where the compound (IIb) is a compound wherein $R^A$ is a dioxolane skeleton, it produces a compound (IIb-30) and it can be led to a known fluorinated resin material by the following production route:

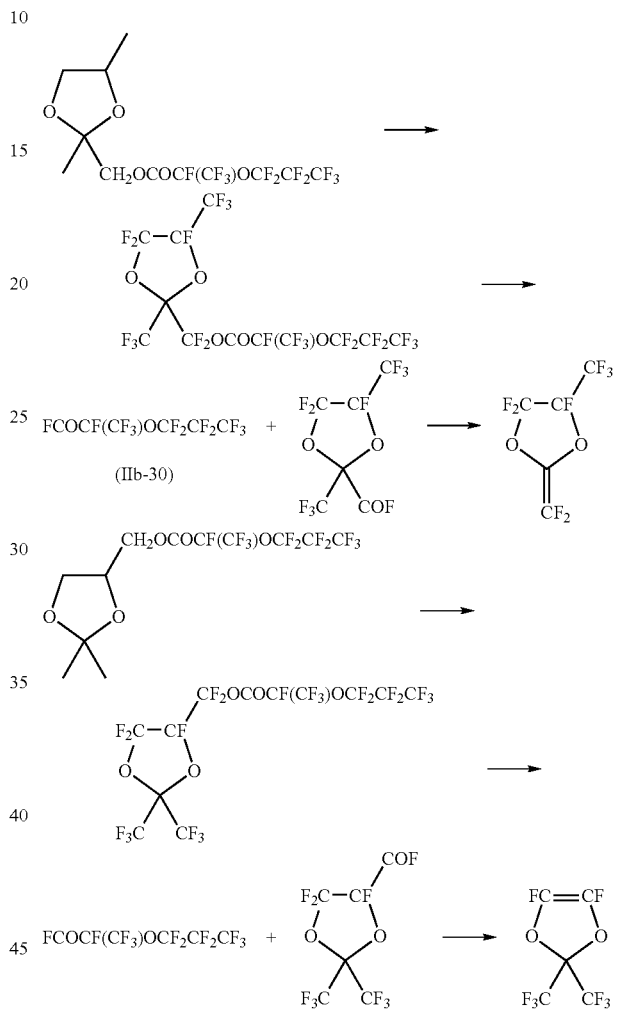

Explanation about Various Production Processes

In the conversion reaction of the compound (IV), the compound (VI) will be formed together with the compound (V). The desired compound in the process for producing of the present invention may be the compound (V) only, the compound (VI) only, or both the compound (V) and the compound (VI).

Further, the process of the present invention can be made to be the following efficient processes 1 to 3 by selecting groups in compounds. In the following, the groups not defined have the same meanings as described above.

Process 1

A process wherein groups are selected so that the compound (V) and the compound (VI) will be the same compound. By this process, the step of separating the product can be omitted.

For example, there may be mentioned a case where groups are selected so that $R^{AF}$ and $R^{BF}$ in the compound (IVd) will be of the same structure, and likewise a case where groups are selected so that $R^{AF1}$ and $R^{BF1}$ in the compound (IVd-1) will be of the same structure. Specific examples of such Process 1 will be exemplified in Process 3.

Process 2

A process wherein a group in the compound (II) is selected so that the resulting compound (VI) will be of the same structure as the compound (II). According to such a process, the resulting compound (VI) (=the compound (II)) can be used again for the reaction with the compound (I), whereby the process of the present invention can be made to be a continuous production process.

A specific example of Process 2 may be an example wherein a perhalogeno group is used as $R^{BF}$ in the compound (IIb). For example, when a compound (IIb-10) is used as the compound (IIb), the process can be made to be the following production process.

Namely, it is a continuous process for producing a compound (Ve) wherein the compound (Ia) and the compound (IIb-10) are reacted to form a compound (IIIc-10); the compound (IIIc-10) is fluorinated in a liquid phase to form a compound (IVd-10); then the compound (IVd-10) is converted (preferably subjected to a thermal decomposition reaction) to obtain a compound (Ve) and a compound (IIb-10), and a part or whole of the compound (IIb-10) is used again for the reaction with the compound (Ia):

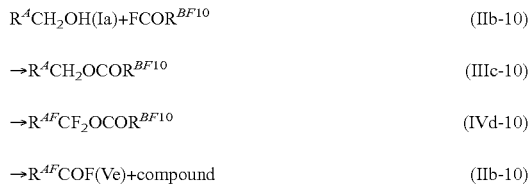

Likewise, it is a continuous process for producing a compound (Ve-1), which comprises a first step of reacting a compound (Ia-1) and a compound (IIb-1) to form a compound (IIIc-1), then reacting the compound (IIIc-1) with fluorine gas in a solvent to form a compound (IVd-1) and then converting (preferably thermally decomposing) the compound (IVd-1) to obtain a compound (IIb-1) together with a compound (Ve-1), a second step of carrying out the same reactions as in the first step by using the compound (IIb-1) obtained by the thermal decomposition in the first step, to obtain a compound (IIb-1) together with the compound (Ve-1), and a further step of repeating the second step by using the compound (IIb-1) obtained by the thermal decomposition in the second step:

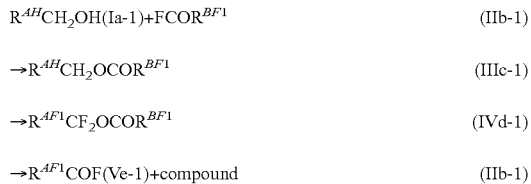

Specifically, it is a continuous process wherein a compound (Ia-2) and a compound (IIb-2) are reacted to form a compound (IIIc-2); the compound (IIIc-2) is fluorinated in a liquid phase to form a compound (IVd-2); the compound (IVd-2) is converted (preferably subjected to a thermal decomposition reaction) to obtain a compound (IIb-2) together with a compound (Ve-2); and then a part or whole of the compound (IIb-2) is used again for the reaction with the compound (Ia-2):

$R^1CH_2OH(Ia-2)+FCOR^2(IIb-2) \rightarrow R^1CH_2OCOR^2$
(IIIc-2)$\rightarrow R^3CF_2OCOR^2$(IVd-2)$\rightarrow R^3COF$(Ve-2)+compound(IIb-2)

Likewise, it is a continuous process wherein in the following production route employing a compound (Ia-30) and a compound (IIb-30), the formed compound (IIb-30) is used again for the reaction with the compound (Ia-30):

$(CH_3)(CH_2ClCHClCH_2CH_2O)CHCH_2OH$(Ia-30)+
$FCOCF(CF_3)(OCF_2CF_2CF_3)$(IIb-30)$\rightarrow$(CH$_3$)
$(CH_2ClCHClCH_2CH_2O)CHCH_2OCOCF(CF_3)$
$(OCF_2CF_2CF_3)$(IIIc-30)$\rightarrow$(CF$_3$)
$(CF_2ClCFClCF_2CF_2O)CFCF_2OCOCF(CF_3)$
$(OCF_2CF_2CF_3)$(IVd-30)$\rightarrow$(CF$_3$)
$(CF_2ClCFClCF_2CF_2O)CFCOF$(IIb-32)+
compound (IIb-30)

The compound (IIb-32) can be led to a material for a fluorine resin [$CF_2=CFCF_2CF_2OCF=CF_2$] by a known method.

Further, in the same manner, it can be made to be a continuous process by using the formed compound (IIb-20) again for the reaction with the compound (Ia-20) in the following production route employing the compound (Ia-20) and the compound (IIb-20):

$CH_2ClCHClCH_2CH_2OH$(Ia-20)+FCOCF$_2$CF$_3$(IIb-20)
$\rightarrow CH_2ClCHClCH_2CH_2OCOCF_2CF_3$(IIIc-40)
$\rightarrow CF_2ClCFClCF_2CF_2OCOCF_2CF_3$(IVd-40)
$\rightarrow FCOCF_2CFClCF_2Cl$(IIb-21)+compound(IIb-20)

Process 3

A process wherein groups are selected so that the resulting compound (V) and the compound (VI) will be of the same structure and further, they will be of the same structure as compound (II). Such a process is particularly preferred since it is unnecessary to separate the product, and a part or whole of the formed compound can be used again for the reaction with the compound (I).

For example, it is a process for producing a compound (Ve-2) wherein a compound (Ia-2) and a compound (Ve-2) are reacted to form a compound (IIIc-4); the compound (IIIc-4) is fluorinated in a liquid phase to form a compound (IVd-4); and then the compound (IVd-4) is converted (preferably thermally decomposed) to obtain a compound (Ve-2). And, it is a continuous process for producing the compound (Ve-2), wherein a part or whole of the formed compound (Ve-2) is used again for the reaction with the compound (Ia-2):

$R^1CH_2OH(Ia-2)+FCOR^3$(Ve-2)$\rightarrow R^1CH_2OCOR_3$(IIIc-4)$\rightarrow R^3CF_2OCOR^3$(IVd-4)$\rightarrow FCOR^3$(Ve-2)

Likewise, it is a continuous process for producing a compound (IIb-31), wherein a compound (Ia-3) and a compound (IIb-31) are reacted to form a compound (IIIc-31); the compound (IIIc-31) is reacted with fluorine gas in a solvent to form a compound (IVd-41); and the compound (IVd-41) is converted (preferably thermally decomposed). And, it is a continuous method for producing the compound (IIb-31), wherein a part or whole of the formed compound (IIb-31) is used again for the reaction with the compound (Ia-3):

$R^4(R^5O)CHCH_2OH$(Ia-3)+FCOCFR$^{80}$(OR$^{90}$)(IIb-31)
$\rightarrow R^4(R^5O)CHCH_2OCOCFR^{80}(OR^{90})$(IIIc-31)
$\rightarrow R^{80}(R^{90}O)CFCF_2OCOCFR^{80}(OR^{90})$(IVd-41)
$\rightarrow$compound(IIb-31)

wherein $R^{80}$: A group corresponding to $R^4$; and when $R^4$ is a group containing no hydrogen atom, the same group as $R^4$, and when $R^4$ is a group containing hydrogen atoms, a group having all of hydrogen atoms in such a group substituted by fluorine atoms;

R$^{90}$: A group corresponding to R$^5$; and when R$^5$ is a group containing no hydrogen atom, the same group as R$^5$, and when R$^5$ is a group containing hydrogen atoms, a group having all of hydrogen atoms in such a group substituted by fluorine atoms.

Specifically, there is a continuous process for producing a compound (IIb-30) represented by the following production route employing a compound (Ia-31) and a compound (IIb-30):

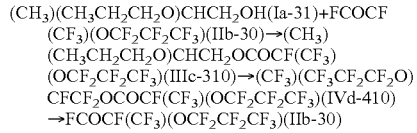

In the above process, the compound (IIIc-310) and the compound (IVd-410) are novel compounds. From the compounds, the compound (IIb-30)) can be obtained. The compound (IIb-30) can be led to perfluoro(propylvinyl ether) which is a fluorinated resin material, by a known method. Further, there is a continuous process for producing a compound (IIb-20) represented by the following production route when a compound (Ia-21) and a compound (IIb-20) are employed:

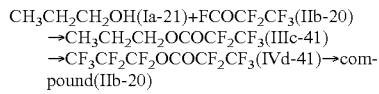

Likewise, specifically, there is a continuous process for producing a compound (IIb-21) represented by the following production route employing a compound (Ia-20) and a compound (IIb-21):

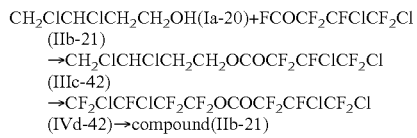

According to the process of the present invention, it is possible to produce various fluorine-containing compounds by using the compound (I) and the compound (II) which are inexpensively available materials. With respect to the compound (I) and the compound (II), various compounds which are different in the structure of R$^A$ or the structure of R$^B$, are commercialized and inexpensively available. And, according to the process of the present invention, from such starting material compounds, a fluorine-containing compound such as an acid fluoride compound can be produced by a short process in good yield. Further, by using the process of the present invention, a low molecular fluorine-containing compound which used to be difficult to obtain by a conventional process, or a fluorine-containing compound having a complex structure, can easily be synthesized. Further, the process of the present invention is a process excellent in wide applicability, which can be applied to various compounds without being limited to the compounds described above as specific examples. Accordingly, a fluorine-containing compound having a desired skeleton can freely be produced. Further, by selecting the structures of R$^A$ and R$^B$, the process of the present invention can be made to be a continuous process.

Further, according to the present invention, a novel acid fluoride compound or its intermediate can be provided which can be used as a fluorinated resin material.

In the foregoing description, the reaction conditions (such as the amounts of the respective compounds to be reacted, the temperatures, the pressures, etc.), etc. in the process of the present invention were specifically described with respect to the compound (Ia), the compound (IIb), the compound (IIIc), the compound (IVd) and the compound (Ve). However, the above-described reaction conditions can be applicable also in cases wherein various compounds included in such compounds, and the compounds (I) to (IV) are employed. Specifically, for example, in the case of the compound (Ia), a compound (Ia-1), a compound (Ia-2) or a compound (Ia-3) may, for example, be mentioned; in the case of the compound (IIb), a compound (IIb-1), a compound (IIb-2) or a compound (IIb-3) may, for example, be mentioned; in the case of the compound (IIIc), a compound (IIIc-1), a compound (IIIc-2) or a compound (IIIc-3) may, for example, be mentioned; in the case of a compound (IVd), a compound (IVd-1), a compound (IVd-2) or a compound (IVd-3) may, for example, be mentioned; and in the case of the compound (Ve), a compound (Ve-1), a compound (Ve-2) or a compound (Ve-3) may, for example, be mentioned.

EXAMPLES

In the following, the present invention will be described in detail with reference to Examples, but the present invention is not limited thereto. Further, in the following, gas chromatography is referred to as GC, and gas chromatography mass spectrometry is referred to as GC-MS. Further, the purity determined from the peak area ratio of GC is referred to as GC purity, and the yield is referred to as GC yield. The yield determined from the peak area ratio of the NMR spectrum will be referred to as NMR yield. Further, tetramethylsilane will be represented by TMS, and CCl$_2$FCClF$_2$ will be represented by R-113. Further, the NMR spectrum data are shown as an apparent chemical shift range. The standard value of the standard material CDCl$_3$ in $^{13}$C-NMR was set to be 76.9 ppm. In the quantitative analysis by $^{19}$F-NMR, C$_6$F$_6$ was employed as the internal standard.

Example 1

Production of CF$_3$(CF$_3$CF$_2$CF$_2$O)CFCOOCH$_2$CH(OCH$_2$CH$_2$CH$_3$) CH$_3$ CH$_3$(CH$_3$CH$_2$CH$_2$O)CHCH$_2$OH (16.5 g) was put into a flask and stirred while bubbling nitrogen gas. CF$_3$(CF$_3$CF$_2$CF$_2$O)CFCOF (46.5 g) was added dropwise thereto over a period of 2 hours while maintaining the internal temperature at from 26 to 31° C. After completion of the dropwise addition, stirring was continued at room temperature for 2 hours, and 50 ml of a saturated sodium hydrogen carbonate aqueous solution was added at an internal temperature of not higher than 15° C. 50 ml of water and 135 ml of chloroform were added thereto, followed by liquid separation to obtain a chloroform layer as an organic layer. Further, the organic layer was washed with 50 ml of water, dried over magnesium sulfate and then subjected to filtration to obtain a crude liquid.

The crude liquid was concentrated by an evaporator, followed by distillation under reduced pressure to obtain a fraction (1) of from 23 to 52° C./4.0 kPa (29 g), a fraction (2) of from 52 to 61° C./from 3.6 to 4.0 kPa (19 g) and a fraction (3) of from 52 to 70° C./from 1.3 to 3.6 kPa (4 g). The GC purity was 68% with the fraction (1), 98% with the fraction (2) and 97% with the fraction (3). The NMR spectrum of the fraction (2) was measured to confirm that the main component was a mixture of diastereomers of CF$_3$CF(OCF$_2$CF$_2$CF$_3$)COOCH$_2$CH(OCH$_2$CH$_2$CH$_3$)CH$_3$.

NMR Spectrum of the Fraction (2)

$^1$H-NMR (399.8 MHz,solvent CDCl$_3$,standard: TMS) δ (ppm): 0.90 (t,J=7.5 Hz, 3H),1.20(d,J=5.4 Hz,3H), 1.50–1.60(m,2H),3.33–3.50(m,2H),3.64–3.74(m,1H), 4.23–4.29(m,1H),4.34–4.41(m,1H).

$^{19}$F-NMR (376.2 MHz,solvent CDCl$_3$,standard: CFCl$_3$) δ (ppm): −80.9(1F),−82.3(3F),−83.1(3F),−87.4(1F),−130.7 (2F),−132.7(1F)

Further, by GC, it was confirmed that the main component contained in the fraction (1) and the fraction (3) was CF$_3$(CF$_3$CF$_2$CF$_2$O)CFCOOCH$_2$CH(OCH$_2$CH$_2$CH$_3$)CH$_3$.

Example 2

Production of CF$_3$(CF$_3$CF$_2$CF$_2$O)CFCOOCF$_2$CF (OCF$_2$CF$_2$CF$_3$)CF$_3$ by a Fluorination Reaction The fraction (2) and the fraction (3) obtained in Example 1 were mixed, and 19.5 g thereof was dissolved in R-113 (250 g) to obtain a fraction solution. On the other hand, into a 500 ml autoclave made of nickel, NaF (26.1 g) was introduced, and R-113 (324 g) was added thereto, followed by stirring and cooling to −10° C. Nitrogen gas was blown thereinto for 1 hour, and then fluorine gas diluted to 20% with nitrogen gas, was blown thereinto for 1 hour at a flow rate of 5.66 l/hr. While blowing it at the same flow rate, the above-mentioned fraction solution was injected over a period of 19.4 hours.

Then, while blowing the fluorine gas diluted to 20% with nitrogen gas at the above-mentioned flow rate, a R-113 solution of benzene (0.01 g/ml) was injected, and the outlet valve of the autoclave was closed, and when the pressure became 0.12 MPa, the inlet valve of the autoclave was closed, whereupon stirring was continued for 1 hour.

Further, such operation was repeated four times during a period where the temperature was raised from −10° C. to room temperature and thereafter five times at room temperature. During this period, benzene was injected in a total amount of 0.291 g and R-113 was injected in a total amount of 45.0 g. Thereafter, nitrogen gas was blown thereinto for 2 hours, and the reaction mixture was taken out by decantation. The obtained crude liquid was concentrated by an evaporator, and the product was quantitatively analyzed by $^{19}$F-NMR, whereby the yield was 69%. A part of the crude liquid was taken and distilled under reduced pressure to obtain purified CF$_3$(CF$_3$CF$_2$CF$_2$O)CFCOOCF$_2$CF (OCF$_2$CF$_2$CF$_3$)CF$_3$. The product was a mixture of diastereomers.

Boiling point: 46 to 51° C./5.2 kPa.

High resolution mass spectrum (CI method) 664.9496 (M+H. theoretical value: C$_{12}$HF$_{24}$O$_4$=664. 9492).

$^{19}$F-NMR (564.6 MHz,solvent CDCl$_3$/C$_6$F$_6$,standard: CFCl$_3$)δ (ppm): −80.6 (1F),−80.8 and −80.9 (3F),−81.6~− 83.1 (2F),−82.6 (6F),−82.8 (3F),−86.7 (1F),−87.4 (1F),− 87.5 (1F),−130.6 (4F),−132.2 (1F),−145.7 and −145.9 (1F).

$^{13}$C-NMR (150.8 MHz,solvent CDCl$_3$/C$_6$F$_6$,standard: CDCl$_3$) δ (ppm): 100.26 and 100.28, 102.8, 106.8, 107.0, 116.0,116.2,116.5 and 116.6,117.4,117.5,117.9,117.9,152.2 and 152.3.

Example 3

Production of CF$_3$(CF$_3$CF$_2$CF$_2$O)CFCOOCF$_2$CF (OCF$_2$CF$_2$CF$_3$)CF$_3$ by a Fluorination Reaction The operation was carried out in the same manner as in Example 2 except that as the solvent, perfluorotributylamine was used instead of R-113, to obtain CF$_3$(CF$_3$CF$_2$CF$_2$O) CFCOOCF$_2$CF(OCF$_2$CF$_2$CF$_3$)CF$_3$. The NMR yield was 70%.

Example 4

Production of CF$_3$CF$_2$COOCH$_2$CH$_2$CH$_3$

CH$_3$CH$_2$CH$_2$OH (268.6 g) was put into a flask and stirred while bubbling nitrogen gas. CF$_3$CF$_2$COF (743 g) was fed over a period of 3.75 hours while maintaining the internal temperature at from 20 to 25° C. After completion of the feeding, stirring was continued for 1.25 hours at room temperature, and 2 l of a saturated sodium hydrogencarbonate aqueous solution was added at an internal temperature of not higher than 20° C. Liquid separation was carried out, and the organic layer was washed with 1 l of water, to obtain a crude liquid (775 g). Then, distillation under reduced pressure was carried out to obtain a fraction (556 g).

Boiling point: 50° C./18.6 kPa.

NMR spectrum of the fraction $^1$H-NMR (399.8 MHz,solvent CDCl$_3$,standard:TMS) δ (ppm): 0.98 (q,J=7.3 Hz,3H),1.76 (m,2H),4.34 (t,J=6.7 Hz,2H).

$^{19}$F-NMR (376.2 MHz,solvent CDCl$_3$,standard:CFCl$_3$) δ (ppm): −84.0 (3F),−122.6 (2F).

Example 5

Production of CF$_3$CF$_2$COOCF$_2$CF$_2$CF$_3$ 12 g of the fraction obtained in Example 4 was dissolved in R-113 (250 g) to obtain a fraction solution. On the other hand, into a 500 ml autoclave made of nickel, R-113 (312 g) was added, followed by stirring and cooling to −10° C. Nitrogen was blown thereinto for 1 hour, and then fluorine gas diluted to 20% with nitrogen gas, was blown thereinto for 1 hour at a flow rate of 5.66 l/hr, and while blowing it at the same flow rate, the fraction solution was injected over a period of 14.75 hours.

Then, while blowing the fluorine gas diluted to 20% with nitrogen gas at the above-described flow rate, a R-113 solution of benzene (0.01 g/ml) was injected, whereupon the outlet valve of the autoclave was closed. When the pressure became 0.12 MPa, the inlet valve of the autoclave was closed, and stirring was continued for 1 hour.

Further, such an operation was repeated three times during a period where the temperature was raised from −10° C. to room temperature and thereafter six times at room temperature. During this period, benzene was injected in a total amount of 0.323 g, and R-113 was injected in a total amount of 50 g. Thereafter, nitrogen gas was blown thereinto for 2 hours. The product was quantitatively analyzed by $^{19}$F-NMR, whereby the yield was 77%.

$^{19}$F-NMR (376.2 MHz,solvent CDCl$_3$,standard:CFCl$_3$) δ (ppm): −82.5 (t,J=7.0 Hz,3F),−83.9 (s,3F),−88.6 (q,J=7.0 Hz,2F),−122.8 (s,2F),−130.9 (s,2F).

Example 6

Production of CF$_3$CF(OCF$_2$CF$_2$CF$_3$)COF by a Liquid Phase Thermal Decomposition CF$_3$CF(OCF$_2$CF$_2$CF$_3$)COOCF$_2$CF(OCF$_2$CF$_2$CF$_3$)CF$_3$ (15 g) obtained in Example 2, was charged into a 100 ml ample made of stainless steel and left to stand in an oven maintained at 200° C. Two hours later, it was taken out and cooled to room temperature, whereupon a liquid sample (14.5 g) was recovered. By GC-MS, it was confirmed that $CF_3CF(OCF_2CF_2CF_3)COF$ was the main product. The NMR yield was 85%.

Example 7

Production of $CF_3CF(OCF_2CF_2CF_3)COF$ by a Gas Phase Thermal Decomposition of $CF_3CF(OCF_2CF_2CF_3)COOCF_2CF(OCF_2CF_2CF_3)CF_3$ An empty U-shaped reactor made of Inconel 600 (internal capacity: 200 ml) was immersed in a salt bath furnace maintained at 250° C. 1 l/hr of nitrogen and $CF_3CF(OCF_2CF_2CF_3)COOCF_2CF(OCF_2CF_2CF_3)CF_3$ obtained in Example 2 were supplied at a flow rate of 15 g/hr from an inlet of the reactor. The retention time was maintained from 10 to 12 seconds. On the outlet side of the reactor, a dry ice/methanol and liquid nitrogen traps were attached to recover the reaction crude gas. After the reaction for 2 hours, a liquid sample (23 g) was recovered from the traps. By GC-MS, it was confirmed that $CF_3CF(OCF_2CF_2CF_3)COF$ was the main product. The NMR yield was 73%.

Example 8

Production of $CF_3CF_2COF$ by a Liquid Phase Thermal Decomposition $CF_3CF_2COOCF_2CF_3$ (20 g) obtained in Example 5 and chlorotrifluoroethylene oligomer (120 g) were charged into a 200 ml autoclave made of nickel and equipped with a reflux condenser and heated to 200° C. The reflux condenser was cooled by circulating cooling water, and when the pressure became at least 0.1 MPa, the gas was purged while maintaining the pressure to recover a gaseous sample (15 g). By GC-MS, it was confirmed that $CF_3CF_2COF$ was the main product. The GC yield was 90%.

Example 9

Production of $CF_3CF_2COOCH_2CH_2CHClCH_2Cl$ $CH_2ClCHClCH_2CH_2OH$ (30 g) was put into a flask and stirred while bubbling nitrogen gas. $CF_3CF_2COF$ (310 g) was fed over a period of 3 hours while maintaining the internal temperature at from 25° C. to 30° C. After completion of the feeding, 50 ml of a saturated sodium hydrogencarbonate aqueous solution was added at an internal temperature of not higher than 15° C. 50 ml of chloroform was added thereto, followed by liquid separation to obtain a chloroform layer as an organic layer. Further, the organic layer was washed twice with 200 ml of water, dried over magnesium sulfate and then subjected to filtration to obtain a crude liquid. The crude liquid was concentrated by an evaporator, and then distilled under reduced pressure to obtain a fraction of from 73 to 75° C./0.9 kPa (24 g). This fraction was purified by silica gel column chromatography (the developing solvent was hexane:ethyl acetate=20:1) to obtain a purified product (18.8 g). The GC purity was 98%. From the NMR spectrum, it was confirmed that the above-identified compound was the main component.

$^1$H-NMR (399.8 MHz,solvent $CDCl_3$,standard: TMS) δ (ppm): 2.11 (m,1H),2.52 (m,1H),3.69 (dd,J=7.9,11.4 Hz,1H),3.84 (dd,J=4.7,11.4 Hz,1H),4.15 (m,1H),4.60 (m,2H).

$^{19}$F-NMR (376.2 MHz,solvent $CDCl_3$,standard:$CFCl_3$) δ (ppm): −83.8 (3F),−122.5 (2F)

Example 10

Production of $CF_3CF_2COOCF_2CF_2CFClCF_2Cl$ by a Fluorination Reaction

Into a 500 ml autoclave made of nickel, R-113 (201 g) was added, followed by stirring and cooling to −10° C. Nitrogen gas was blown thereinto for 1 hour, and then fluorine gas diluted to 20% with nitrogen gas, was blown thereinto for 1 hour at a flow rate of 5.66 l/hr. While blowing the fluorine gas at the same flow rate, a solution having $CF_3CF_2COOCH_2CH_2CHClCH_2Cl$ (6.58 g) obtained in Example 9 dissolved in R-113 (134 g), was injected over a period of 6.9 hours.

Then, while blowing the fluorine gas at the same flow rate, a R-113 solution of benzene (0.01 g/ml) was injected, whereupon the outlet valve of the autoclave was closed. When the pressure became 0.12 MPa, the inlet valve of the autoclave was closed, and stirring was continued for 1 hour. Further, the same operation of injecting benzene was repeated once while raising the temperature from −10° C. to 40° C. and then eight times at 40° C. The total amount of benzene injected was 0.330 g, and the total amount of R-113 injected was 33 ml. Further, nitrogen gas was blown thereinto for 2 hours. The product was quantitatively analyzed by $^{19}$F-NMR, whereby the yield of the above-identified compound was 51%.

$^{19}$F-NMR (376.2 MHz,solvent $CDCl_3$,standard:$CFCl_3$) δ (ppm): −65.4 (2F),−84.2 (3F),−85.4 (2F),−119.1 (2F),−123.1 (2F),−132.5 (1F).

Example 11

Production of a Mixture of $CF_2ClCFClCF_2COOCH_2CH_2CHClCH_2C_1$ and $CF_2ClCF_2CFClCOOCH_2CH_2CHClCH_2Cl$ $CH_2ClCHClCH_2CH_2OH$ (49.5 g) was put into a flask and stirred while bubbling nitrogen gas. A mixture (86.1 g) of $CF_2ClCFClCF_2COF$ and $CF_2ClCF_2CFClCOF$ in 89:11 (molar ratio) was added dropwise over a period of 1 hour and 40 minutes while maintaining the internal temperature at from 25 to 30° C. After completion of the dropwise addition, stirring was continued at room temperature for 2 hours and 45 minutes, and a saturated sodium hydrogencarbonate aqueous solution (100 ml) was added thereto while keeping the internal temperature not to exceed 15° C. 150 ml of chloroform was added thereto, followed by liquid separation to obtain a chloroform layer. Further, the chloroform layer was washed twice with 200 ml of water, dried over magnesium sulfate and then subjected to filtration to obtain a crude liquid. The crude liquid was concentrated by an evaporator and then distilled under reduced pressure to obtain a fraction (1) of from 99 to 106° C./0.48 kPa (55.4 g), a fraction (2) of from 100 to 109° C./0.47 kPa (7.9 g). The GC purity as the above mixture was 85% with the fraction (1) and 84% with the fraction (2).

The fraction (1) (9.4 g) was purified by silica gel column chromatography (the developing solvent was hexane:ethyl acetate=20:1) to obtain a purified product (7.5 g). The GC purity of the purified product was 98%. From the NMR spectrum of the purified product, it was confirmed that a mixture of $CF_2ClCFClCF_2COOCH_2CH_2CHClCH_2C_1$ and $CF_2ClCF_2CFClCOOCH_2CH_2CHClCH_2Cl$ was the main component, and their ratio was 87:13 (molar ratio).

$CF_2ClCFClCF_2COOCH_2CH_2CHClCH_2Cl$:

$^1$H-NMR (399.8 MHz,solvent CDCl$_3$,standard:TMS) δ (ppm): 2.09 (m,1H),2.52 (m,1H),3.69 (dd,J=7.6,11.4 Hz,1H) 3.84 (dd,J=4.7,11.4 Hz,1H),4.17 (m,1H),4.58 (m,2H).

$^{19}$F-NMR (376.2 MHz,solvent CDCl$_3$,standard: CFCl$_3$) δ (ppm): −63.6 (1F),−64.8 (1F),−110.9 (1F),−114.0 (1F),−131 (1F).

$CF_2ClCF_2CFClCOOCH_2CH_2CHClCH_2Cl$:

$^1$H-NMR (399.8 MHz,solvent CDCl$_3$,standard:TMS) δ (ppm): 2.09 (m,1H),2.52 (m,1H),3.69 (dd,J=7.6,11.4 Hz,1H),3.84 (dd,J=4.7,11.4 Hz,1H),4.17 (m,1H),4.58 (m,2H).

$^{19}$F-NMR (376.2 MHz,solvent CDCl$_3$,standard:CFCl$_3$) δ (ppm) 66.9 (1F),−67.0 (1F),−113.4 (1F),−117.6 (1F),−129.0 (1F).

Example 12

Production of a Mixture of $CF_2ClCFClCF_2COOCF_2CF_2CFClCF_2C_1$ and $CF_2ClCF_2CFClCOOCF_2CF_2CFClCF_2Cl$ by a fluorination reaction Into a 500 ml autoclave made of nickel, R-113 (200 g) was added and stirred, and nitrogen gas was blown thereinto at room temperature for 1 hour. Then, fluorine gas diluted to 20% with nitrogen gas, was blown thereinto for 1 hour at a room temperature at a flow rate of 5.66 l/hr.

Then, while blowing the fluorine gas at the same flow rate, a solution having a mixture (12 g) of $CF_2ClCFClCF_2COOCH_2CH_2CHClCH_2C_1$ and $CF_2ClCF_2CFClCOOCH_2CH_2CHClCH_2Cl$ obtained in Example 1 in 87:13 (molar ratio) dissolved in R-113 (243 g), was injected over a period of 11.5 hours.

Then, while blowing the fluorine gas at the same flow rate, a R-113 solution of benzene (0.01 g/ml) was injected, whereupon the outlet valve of the autoclave was closed. When the pressure became 0.12 MPa, the inlet valve of the autoclave was closed, and stirring was continued for 1 hour. Further, the same operation of injecting benzene was repeated once while raising the temperature from room temperature to 40° C. and then eight times at 40° C. The total amount of benzene injected was 0.342 g, and the total amount of R-113 injected was 33 ml. Further, nitrogen gas was blown thereinto for 2 hours. The yield of the above-identified mixture obtained from the $^{19}$F-NMR spectrum (internal standard: $C_6F_6$) of the product was 80%.

$CF_2ClCFClCF_2COOCF_2CF_2CFClCF_2Cl$:

$^{19}$F-NMR (564.6 MHz,solvent CDCl$_3$,standard:CFCl$_3$) δ (ppm): −64.4~−65.9 (2F),−65.4 (2F),−85.5~−86.3 (2F),−111.1 ~−115.1 (2F),−118.7~−120.1 (2F),−132.0 (1F),−132.5 (1F).

$^{13}$C-NMR (150.8 MHz,solvent CDCl$_3$,standard:CDCl$_3$) δ (ppm): 104.4,104.5,109.4,110.8,116.6,124.3,124.6,152.0.

$CF_2ClCF_2CFClCOOCF_2CF_2CFClCF_2Cl$:

$^{19}$F-NMR (564.6 MHz,solvent CDCl$_3$,standard:CFCl$_3$) δ (ppm): −64.4~−66.0 (2F),−68.0 (2F),−85.5~−86.3 (2F),−113.7~−115.3 (2F),−118.7~−120.1 (2F),−130.0 (1F),−132.5 (1F).

$^{13}$C-NMR (150.8 MHz,solvent CDCl$_3$,standard:CDCl$_3$) δ (ppm): 99.0,104.4,110.2,110.8,116.6,122.8,124.6,153.2.

Example 13

Production of $CH_3CHClCOOCH_2Cy$

Into a 200 ml three-necked flask, 2-chloropropionic acid (28.5 g), cyclohexane methanol (30.0 g), sulfuric acid (5 ml) and toluene (75 ml) were charged and stirred. The mixture was heated until the internal temperature became 117° C. and then left to cool.

The reaction mixture was added to a saturated sodium carbonate aqueous solution (170 ml), whereupon the liquid separated into 2 layers were separated. From the aqueous layer, an organic substance was extracted with toluene (100 ml) and put together with the organic layer, followed by drying over sodium carbonate. After the filtration, toluene was distilled off to obtain a crude product (52.4 g). This product was distilled under reduced pressure to obtain $CH_3CHClCOOCH_2Cy$ (45.9 g) as a fraction having a GC purity of at least 94%.

Boiling point: 140 to 142° C./4.5 to 4.7 kPa $^1$H-NMR (300.40 MHz,solvent:CDCl$_3$,standard:TMS)δ (ppm): 0.90~1.03 (m,2H),1.07~1.32 (m,3H),1.60~1.72 (m,6H),1.68 (d,J=6.9 Hz,3H),3.97 (dd,J=2.7,6.3 Hz,2H),4.38 (q,J=6.9 Hz,1H).

Example 14

Production of $CH_3CH(OCH_2Cy)COOCH_2Cy$

Into a 300 ml four-necked flask, N,N-dimethylformamide (70 ml) and sodium hydride (60%, 9.77 g) were charged and stirred, and $HOCH_2Cy$ (25.1 g) was added dropwise under cooling with ice. After completion of the dropwise addition, stirring was continued at room temperature for 1 hour. Then, $CH_3CHClCOOCH_2Cy$ (45.0 g) obtained in Example 13 was added dropwise over a period of 100 minutes while suitably cooling so that the internal temperature was maintained at a level of not higher than 40° C. After completion of the dropwise addition, stirring was continued for 3 hours at a bath temperature of 88° C. After cooling, 2 mol/Q hydrochloric acid (50 ml) was added dropwise over a period of 8 minutes under cooling with ice, and then the mixture was added to 2 mol/Q hydrochloric acid (150 ml). It was extracted with a mixture (400 ml) of hexane:ethyl acetate=2:1, and the organic layer was washed twice with water (100 ml). The organic layer was dried over magnesium sulfate, and the solvent was distilled off to obtain a residue (64.0 g). This residue was distilled under reduced pressure to obtain $CH_3CH(OCH_2Cy)COOCH_2Cy$ (44.4 g) having a GC purity of 96.8%.

Boiling point: 120 to 138° C./0.70 to 0.80 kPa.

$^1$H-NMR (300.40 MHz,solvent:CDCl$_3$,standard:TMS) δ (ppm): 0.77~1.03 (m,4H),1.03~1.31 (m,6H),1.36 (d,J=4.8 Hz,3H),1.47~1.82 (m,12H),3.11 (dd,J=6.6,9.0 Hz,1H),3.33 (dd,J=6.6,9.0 Hz,1H),3.82~3.99 (m,3H).

Example 15

Production of $CH_3CH(OCH_2Cy)CH_2OH$

In a nitrogen stream, into a 500 ml four-necked flask, toluene (150 ml) and bis(2-methoxyethoxy)aluminum sodium hydride (65% toluene solution, 175.1 g) were charged and stirred, and $CH_3CH(OCH_2Cy)COOCH_2Cy$ (30.0 g) obtained in Example 14 was added dropwise over a period of 70 minutes at an internal temperature of not higher than 45° C. Stirring was continued for 1.5 hours at an internal temperature of 85° C., followed by cooling in an ice bath to an internal temperature of 2.2° C., whereupon 26 ml of 2 mol/Q hydrochloric acid was added dropwise thereto.

The reaction mixture was added to 1500 ml of 2 mol/l hydrochloric acid, and extracted with t-butylmethyl ether (700 ml). From the aqueous layer subjected to liquid separation, an organic substance was further extracted with t-butylmethyl ether (200 ml) and put together with the organic layer, followed by washing with water (150 ml). The organic layer was dried over magnesium sulfate and subjected to filtration, and the solvent was distilled off to obtain a crude product (29.3 g). This crude product was distilled under reduced pressure to obtain $CH_3CH(OCH_2Cy)CH_2OH$ (14.6 g) having a GC purity of 98.9 g.

Boiling point: 112 to 128° C./3.2 to 3.3 kPa.

$^1$H-NMR (300.40 MHz,solvent:CDCl$_3$,standard:TMS) δ (ppm): 0.85~1.03 (m,2H),1.10 (d,J=6.0 Hz,3H),1.12~1.34 (m,3H),1.48~1.82 (m,6H),2.08 (dd,J=3.9,8.1 Hz,1H),3.17 (dd,J=6.8,9.0 Hz,1H), 3.33~3.62 (m,4H).

Example 16

Production of $CH_3CH(OCH_2Cy)$ $CH_2OCOCF(CF_3)$ $OCF_2CF_3$ $CH_3CH(OCH_2Cy)CH_2OH$ (13.8 g) having a GC purity of 98% obtained in Example 15, was put into a flask and stirred while bubbling nitrogen gas. $FCOCF(CF_3)OCF_2CF_3$ (32 g) was added dropwise over a period of 30 minutes while maintaining the internal temperature at from 25 to 30° C. After completion of the dropwise addition, stirring was continued at room temperature for 3 hours, and 50 ml of a saturated sodium hydrogencarbonate aqueous solution was added at an internal temperature of not higher than 15° C.

The obtained crude liquid was subjected to liquid separation, and the lower layer was washed twice with 50 ml of water, dried over magnesium sulfate and then subjected to filtration to obtain a crude liquid. The crude liquid was purified by silica gel column chromatography (developing solvent: dichloropentafluoropropane (tradename: AK-225)), to obtain $CH_3CH(OCH_2Cy)$ $CH_2OCOCF(CF_3)$ $OCF_2CF_3$ (15.4 g). The GC purity was 99%.

$^1$H-NMR (399.8 MHz,solvent: CDCl$_3$,standard:TMS) δ (ppm): 0.82–0.95 (m,2H),1.07~1.28 (m,3H),1.17,1.17 (d,J=6.4 Hz,d,J=6.4 Hz,3H),1.44~1.55 (m,1H),1.61~1.75 (m,5H),3.20,3.28 (dd,J=6.8,8.8 Hz,ddd,J=3.2,6.4,8.8 Hz,2H),3.60~3.68 (m,1H),4.21~4.26,4.32~4.40 (m,2H).

$^{19}$F-NMR (376.2 MHz,solvent:CDCl$_3$,standard:CFCl$_3$) δ (ppm): −80.4 (1F),−81.8 (3F),−82.5 (3F),−86.8 (1F),−130.2 (2F),−132.1 (1F).

Example 17

Production of $CY^FCF_2OCF(CF_3)CF_2OCOCF(CF_3)$ $OCF_2CF_3$

Into a 500 ml autoclave made of nickel, R-113 (312 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1 hour, and then fluorine gas diluted to 20% with nitrogen gas, was blown thereinto for 1 hour at a flow rate of 8.63 l/hr. Then, while blowing the fluorine gas at the same flow rate, a solution having $CyCH_2OCH(CH_3)$ $CH_2OCOCF(CF_3)OCF_2CF_3$ (4.98 g) obtained in Example 16 dissolved in R-113 (100 g), was injected over a period of 7.8 hours.

Then, while blowing the fluorine gas at the same flow rate, the internal pressure of the autoclave was raised to 0.15 MPa, and a R-113 solution having a benzene concentration of 0.01 g/ml, was injected in an amount of 6 ml while raising the temperature from 25° C. to 40° C., whereupon the benzene injection inlet of the autoclave was closed, and stirring was continued for 0.3 hour.

Then, while maintaining the internal pressure of the reactor at 0.15 MPa and the internal temperature of the reactor at 40° C., 3 ml of the above-mentioned benzene solution was injected, whereupon the benzene injection inlet of the autoclave was closed, and stirring was continued for 0.3 hour. Further, the same operation was repeated three times. The total amount of benzene injected was 0.184 g, the total amount of R-113 injected was 18 ml. Further, while blowing the fluorine gas at the same flow rate, stirring was continued for 0.8 hour.

Then, the internal pressure of the reactor was adjusted to be atmospheric pressure, and nitrogen gas was blown thereinto for 1.5 hours. The desired product was quantitatively analyzed by $^{19}$F-NMR, whereby the yield of the above-identified compound was 75%.

$^{19}$F-NMR (376.0 MHz,solvent:CDCl$_3$,standard:CFCl$_3$) δ (ppm): −68.1~−70.4 (2F),−80.4—81.1(4F),−82.4 (3F),−82.7 (3F),−87.0 (1F),−87.4 (2F),−119.5—143.5 (10F),−130.6 (2F),−132.7 (1F),−146.0 and −146.3 (1F),−187.9 (1F)

Example 18

Production of $Cy^FCF_2OCF(CF_3)COF$ $Cy^FCF_2OCF(CF_3)CF_2OCOCF(CF_3)OCF_2CF_3$ (0.9 g) obtained in Example 17, was charged into a flask together with a NaF powder (0.01 g) and heated at 120° C. for 5.5 hours and at 140° C. for 5 hours in an oil bath with vigorous stirring. At an upper portion of the flask, a reflux condenser adjusted at a temperature of 20° C., was installed. After cooling, the liquid sample (0.9 g) was recovered. By GC-MS, it was confirmed that $CF_3CF(OCF_2CF_2CF_3)COF$ and the above-identified compound were the main products. The NMR yield was 66.0%.

$^{19}$F-NMR (376.0 MHz,solvent:CDCl$_3$,standard:CFCl$_3$) δ (ppm): 25.8 (1F),−67.4 (1F),−75.6 (1F),−82.4(3F),−119.5~−143.5 (10F),−132.4 (1F),−187.9 (1F)

Example 19

Production of $CH_3CHClCOO(CH_2)_9CH_3$

Into a 500 ml four-necked flask, triethylamine (68.4 g) and 1-decanol (51.0 g) were charged and stirred, and while maintaining the internal temperature at a level of not higher than 12° C., 2-chloropropionyl chloride (42.9 g) was added dropwise over a period of 75 minutes under cooling with ice. The mixture was diluted with dichloromethane (50 ml) and stirred for 30 minutes. The reaction mixture was added to water (400 ml) for liquid separation into two layers. An organic substance was extracted from the aqueous layer with dichloromethane (100 ml) and put together with the organic layer. The above operation was carried out in one more batch in a scale of 1-decanol (8.4 g), and the organic layers of the two batches were put together and washed with water (400 ml, 300 ml) and dichloromethane (100 ml) was added thereto, followed by liquid separation.

The organic layer was dried over magnesium sulfate and filtered, and then the solvent was distilled off to obtain a residue (86.6 g). This residue was distilled under reduced pressure to obtain $CH_3CHClCOO(CH_2)_9CH_3$ (64.8 g) having a GC purity of 89.9%.

Boiling point: 135 to 139° C./0.63 to 0.67 kPa $^1$H-NMR (300.40 MHz,solvent:CDCl$_3$,standard:TMS) δ (ppm): 0.88 (t,J=6.9 Hz,3H),1.3~1.5 (m,14H),1.6–1.7 (m,2H),1.77 (d,J=6.9 Hz,3H),4.1~4.2 (m,2H),4.39 (q,J=6.9 Hz,1H)

Example 20

Production of $CH_3CH(O(CH_2)_9CH_3)COO(CH_2)_9CH_3$

Into a 500 ml eggplant type flask, 1-decanol (180 g) and a methanol solution of sodium methylate (28%) were charged, stirred and heated under reduced pressure to distill off methanol. By GC, it was confirmed that no methanol remained in the reaction solution. Into a 1 l four-necked flask, N,N-dimethylformamide (150 ml) and $CH_3CHClCOO(CH_2)_9CH_3$ (27.1 g) obtained in Example 19 were charged and stirred, and a solution of sodium decylate obtained in the above operation was added dropwise at an internal temperature of not higher than 25° C. The mixture was heated to an internal temperature of 70° C. and stirred for 30 minutes.

This was carried out in two batches, and the reaction crude liquids put together were washed three times with water (200 ml). An organic substance was extracted from the aqueous layer with a mixed liquid (450 ml) of hexane:ethyl acetate=2:1 and put together with the organic layer, and the solvent and 1-decanol were distilled off from the organic layer to obtain $CH_3CH(O(CH_2)_9CH_3)COO(CH_2)_9CH_3$ (70.8 g) having a GC purity of 90.0%.

$^1$H-NMR (300.40 MHz,solvent:CDCl$_3$,standard:TMS) δ (ppm): 0.88 (t,J=7.2 Hz,6H),1.2~1.5 (m,28H),1.44 (d,J=7.5 Hz,3H),1.5~1.7 (m,4H),3.3~3.4 (m,1H),3.5~3.6 (m,1H), 3.93(q,J=6.9 Hz,1H),4.0~4.2 (m,2H).

Example 21

Production of $CH_3CH(O(CH_2)_9CH_3)CH_2OH$

In a nitrogen stream, into a 1 l four-necked flask, toluene (300 ml) and bis(2-methoxyethoxy)aluminum sodium hydride (65% toluene solution, 214 g) were charged and stirred, and $CH_3CH(O(CH_2)_9CH_3)COO(CH_2)_9CH_3$ (30.0 g) obtained in Example 20 was added dropwise over a period of 45 minutes at an internal temperature of not higher than 20° C. The mixture was stirred for 1.5 hours at an internal temperature of 90° C. and then cooled in an ice bath, whereupon 20 ml of 2 mol/l hydrochloric acid was added dropwise.

The reaction mixture was added to 1000 ml of 2 mol/l hydrochloric acid and extracted with t-butylmethyl ether (800 ml). From the aqueous layer subjected to liquid separation, an organic substance was extracted with t-butylmethyl ether (400 ml) and put together with the organic layer.

The organic layer was dried over magnesium sulfate and subjected to filtration, and then, the solvent was distilled off to obtain a crude product (63.4 g). Under reduced pressure and heating, the solvent and 1-decanol were distilled off to obtain $CH_3CH(O(CH_2)_9CH_3)CH_2OH$ (16.0 g) having a GC purity of 97%.

$^1$H-NMR (300.40 MHz,solvent:CDCl$_3$,standard:TMS) δ (ppm): 0.88 (t,J=6.9 Hz,3H),1.09 (d,J=6.3 Hz,3H),1.2~1.4 (m,14H),1.5~1.7 (m,2H),2.1 (bs,1H),3.3~3.6 (m,5H).

Example 22

Production of $CH_3CH(O(CH_2)_9CH_3)CH_2OCOCF(CF_3)OCF_2CF_2CF_3$ $CH_3CH(O(CH_2)_9CH_3)CH_2OH$ (15.5 g) having a GC purity of 97% obtained in Example 21 and triethylamine (15.2 g) were put into a flask and stirred in an ice bath. $FCOCF(CF_3)OCF_2CF_2CF_3$ (32 g) was added dropwise over a period of 30 minutes while maintaining the internal temperature at a level of not higher than 10° C. After completion of the dropwise addition, the mixture was adjusted to room temperature, stirred for 2 hours and then added to 100 ml of ice water.

The obtained crude liquid was subjected to liquid separation, and the lower layer was washed twice with 100 ml of water, dried over magnesium sulfate and then subjected to filtration to obtain a crude liquid. The crude liquid was purified by silica gel column chromatography (developing solvent: AK-225) to obtain $CH_3CH(O(CH_2)_9CH_3)CH_2OCOCF(CF_3)OCF_2CF_2CF_3$ (23.2 g). The GC purity was 96%.

$^1$H-NMR (300.4 MHz,solvent:CDCl$_3$,standard:TMS) δ (ppm): 0.87 (t,J=6.6 Hz,3H),1.18,1.19 (d,J=6.3 Hz,d,J=6.3 Hz,3H),1.21~1.32 (m,14H),1.47~1.54 (m,2H),3.36~3.52 (m,2H),3.62~3.72 (m,1H),4.22–4.28,4.33~4.40 (m,2H).

$^{19}$F-NMR (282.7 MHz,solvent CDCl$_3$,standard:CFCl$_3$) δ (ppm): −80.0 (1F),−81.3 (3F),−82.1 (3F),−86.4 (1F),−129.5 (2F),−131.5 (1F).

Example 23

Production of $CF_3(CF_2)_9OCF(CF_3)CF_2OCOCF(CF_3)OCF_2CF_2CF_3$

Into a 500 ml autoclave made of nickel, R-113 (312 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1 hour, and then fluorine gas diluted to 20% with nitrogen gas, was blown thereinto for 1 hour at a flow rate of 10.33 l/hr.

Then, while blowing the fluorine gas at the same flow rate, a solution having $CH_3(CH_2)_9OCH(CH_3)CH_2OCOCF(CF_3)OCF_2CF_2CF_3$ (4.81 g) obtained in Example 22 dissolved in R-113 (100 g), was injected over a period of 8.0 hours. Then, while blowing the fluorine gas at the same flow rate, a R-113 solution having a benzene concentration of 0.01 g/ml was injected in an amount of 6 ml while raising the temperature from 25° C. to 40° C. and while raising the internal pressure of the autoclave to 0.15 MPa, whereupon the benzene injection inlet of the autoclave was closed, and stirring was continued for 0.3 hour. Then, while maintaining the internal pressure of the reactor at 0.15 MPa and the internal temperature of the reactor at 40° C., 3 ml of the above-mentioned benzene solution was injected, whereupon the benzene injection inlet of the autoclave was closed, and stirring was continued for 0.3 hour. Further, the same operation was repeated three times. The total amount of benzene injected was 0.183 g, the total amount of R-113 injected was 18 ml.

Further, while blowing the fluorine gas at the same flow rate, stirring was continued for 0.8 hour. Then, the internal pressure of the reactor was adjusted to atmospheric pressure, and nitrogen gas was blown thereinto for 1.5 hours. The desired product was quantitatively analyzed by $^{19}$F-NMR, whereby the yield of the above-identified compound was 69%.

$^{19}$F-NMR (376.0 MHz,solvent:CDCl$_3$,standard:CFCl$_3$) δ (ppm): −80.2∼−81.6 (4F),−81.8 (2F),−82.3 (6F),−82.6 (3F),−86.5∼−88.6 (3F),−122.5 (8F),−122.8 (2F),−123.0 (2F),−125.8 (2F),−126.9 (2F),−130.5 (2F),−132.4 (1F),−145.7 and −146.0 (1F).

Example 24

Production of CF$_3$(CF$_2$)$_9$OCF(CF$_3$)COF

CF$_3$(CF$_2$)$_9$OCF(CF$_3$)CF$_2$OCOCF(CF$_3$)OCF$_2$CF$_2$CF$_3$ (2.0 g) obtained in Example 23 was charged into a flask together with a NaF powder (0.05 g) and heated at 150° C. for 24 hours in an oil bath with vigorous stirring. At an upper part of the flask, a reflux condenser adjusted to a temperature of 20° C., was installed. After cooling, the liquid sample (1.9 g) was recovered. By GC-MS, it was confirmed that CF$_3$CF(OCF$_2$CF$_3$)COF and the above-identified compound were the main products. The yield was 63.8%.

Mass spectrum (CI method): 683 (M+H)

Example 25

Production of Compound (IIIc-50)

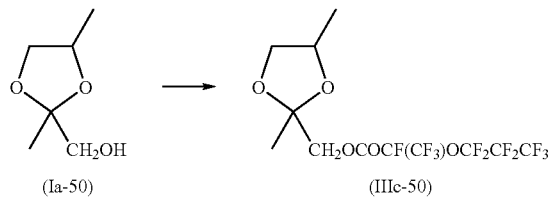

(Ia-50)      (IIIc-50)

A compound (Ia-50) (22.7 g) and triethylamine (36.5 g) were put into a flask and stirred in an ice bath. FCOCF(CF$_3$)OCF$_2$CF$_2$CF$_3$ (60 g) was added dropwise over a period of 1 hour while maintaining the internal temperature at a level of not higher than 10° C. After completion of the dropwise addition, stirring was continued at room temperature for 2 hours, and the mixture was added to 100 ml of ice water.

The obtained crude liquid was subjected to liquid separation, and the lower layer was washed twice with 100 ml of water, dried over magnesium sulfate and then subjected to filtration to obtain a crude liquid. The crude liquid was distilled under reduced pressure to obtain a compound (IIIc-50) (23.4 g) as a fraction of from 87.5 to 88.5° C./1.4 kPa. The GC purity was 99%.

$^1$H-NMR (300.4 MHz,solvent:CDCl$_3$,standard:TMS) δ (ppm): 1.24,1.25 (d,J=6.0 Hz,dd,J=1.2,6.0 Hz,3H) 1.36,1.41 (s, 3H),3.39∼3.49 (m,1H),4.03∼4.42 (m,4H).

$^{19}$F-NMR (282.7 MHz,solvent:CDCl$_3$,standard:CFCl$_3$) δ (ppm): −80.0 (1F),−81.4 (3F),−82.0∼−82.1(3F),−85.8∼−86.6 (1F),−129.5 (2F),−131.4∼−131.7 (1F).

Example 26

Production of Compound (IVd-50)

Into a 500 ml autoclave made of nickel, R-113 (313 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave.

Nitrogen gas was blown thereinto for 1.3 hours, and then fluorine gas diluted to 20% with nitrogen gas, was blown thereinto for 1 hour at a flow rate of 7.87 l/hr. Then, while blowing the fluorine gas at the same flow rate, a solution having the compound (IIIc-50) (4.96 g) obtained in Example 25 dissolved in R-113 (100 g), was injected over a period of 5.3 hours.

Then, while blowing the fluorine gas at the same flow rate, a R-113 solution having a benzene concentration of 0.01 g/ml, was injected in an amount of 9 ml while raising the temperature from 25° C. to 40° C., whereupon the benzene injection inlet of the autoclave was closed, and the outlet valve of the autoclave was closed. When the pressure became 0.20 MPa, the fluorine gas inlet valve of the autoclave was closed, and stirring was continued for 0.6 hour.

Then, the pressure was adjusted to atmospheric pressure, and while maintaining the internal temperature of the reactor at 40° C., 6 ml of the above-mentioned benzene solution was injected, whereupon the benzene injection inlet of the autoclave was closed, and further, the outlet valve of the autoclave was closed. When the pressure became 0.20 MPa, the fluorine gas inlet valve of the autoclave was closed, and stirring was continued for 0.6 hour. Further, the same operation was repeated three times. The total amount of benzene injected was 0.347 g, and the total amount of R-113 injected was 33 ml. Further, nitrogen gas was blown thereinto for 1.5 hours. The desired product was quantitatively analyzed by $^{19}$F-NMR, whereby the yield of the above-identified compound was 87%.

$^{19}$F-NMR (376.0 MHz,solvent:CDCl$_3$,standard:CFCl$_3$) δ (ppm): −78.3 (1F),−80.0∼−80.9 (4F),−81.4 (3F),−81.5∼−82.5 (1F),−82.4 (3F),−82.6 (3F),−86.5∼88.1 (3F),−123.7 (1F),−130.6 (2F),−132.7 (1F).

Example 27

Production of Compound (Ve-50)

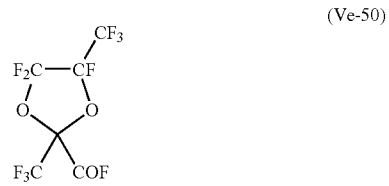

The compound (IVd-50) (2.1 g) obtained in Example 26 was charged into a flask together with a NaF powder (0.02 g) and heated for 10 hours at 120° C. in an oil bath with vigorous stirring. At an upper portion of the flask, a reflux condenser adjusted to a temperature of 20° C., was installed. After cooling, a liquid sample (2.0 g) was recovered. By GC-MS, it was confirmed that CF$_3$CF(OCF$_2$CF$_2$CF$_3$)COF and the above-identified compound were the main products. The NMR yield was 71.2%.

$^{19}$F-NMR (282.7 MHz,solvent:CDCl$_3$,standard:CFCl$_3$) δ (ppm): 24.3 and 23.7 (1F),−77.8~−79.0 (1F),−80.0 and 80.2(3F),−81.3 (3F),−83.3 and −83.8 (1F),−123.9 and −124.9 (1F).

Example 28

Production of Compound (IIIc-51)

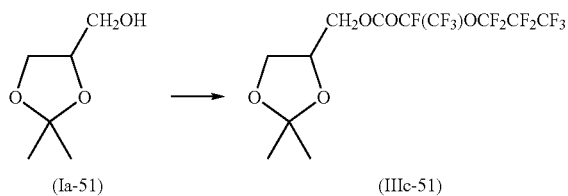

A compound (Ia-51) (15 g) was put into a flask and stirred while bubbling nitrogen gas. FCOCF(CF$_3$)OCF$_2$CF$_2$CF$_3$ (40 g) was added dropwise over a period of 30 minutes while maintaining the internal temperature from 25 to 30° C. After completion of the dropwise addition, stirring was continued at room temperature for 3 hours, and 50 ml of a saturated sodium hydrogencarbonate aqueous solution was added at an internal temperature of not higher than 15° C.

The obtained crude oil was subjected to liquid separation, and the lower layer was washed twice with 50 ml of water, dried over magnesium sulfate and then subjected to filtration to obtain a crude liquid. The crude liquid was distilled under reduced pressure to obtain a compound (IIIc-51) (11.3 g) as a fraction of from 99 to 100° C./2.7 kPa. The GC purity was 99%.

$^1$H-NMR (399.8 MHz,solvent:CDCl$_3$,standard:TMS) δ (ppm): 1.36,1.42 (s,6H),3.78,4.10 (dt,J=5.2,8.8 Hz,dd,J=6.4, 8.8 Hz,2H),4.31~4.51 (m,3H)

$^{19}$F-NMR (376.2 MHz,solvent:CDCl$_3$,standard:CFCl$_3$) δ (ppm): −80.3 (1F),−81.8(3F),−82.6(3F),−87.0 (1F),−130.2 (2F),−132.2 (1F).

Example 29

Production of Compound (IVd-51)

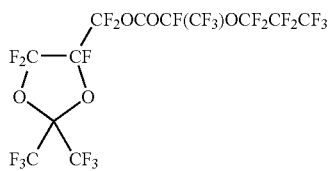

Into a 500 ml autoclave made of nickel, R-113 (312 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1.0 hour, fluorine gas diluted to 20% with nitrogen gas, was blown thereinto for 1 hour at a flow rate of 7.71 l/hr. Then, while blowing the fluorine gas at the same flow rate, a solution having the compound (IIIc-51) (5.01 g) obtained in Example 28 dissolved in R-113 (100 g), was injected over a period of 5.6 hours.

Then, while blowing the fluorine gas at the same flow rate, a R-113 solution having a benzene concentration of 0.01 g/ml, was injected in an amount of 9 ml while raising the temperature from 25° C. to 40° C., whereupon the benzene injection inlet of the autoclave was closed, and further the outlet valve of the autoclave was closed. When the pressure became 0.20 MPa, the fluorine gas inlet valve of the autoclave was closed, and stirring was continued for 0.9 hour.

Then, the pressure was adjusted to atmospheric pressure, and while maintaining the internal temperature of the reactor at 40° C., 6 ml of the above-mentioned benzene solution was injected, whereupon the benzene injection inlet of the autoclave was closed, and further the outlet valve of the autoclave was closed. When the pressure became 0.20 MPa, the fluorine gas inlet valve of the autoclave was closed, and stirring was continued for 0.8 hour. Further, the same operation was repeated three times. The total amount of benzene injected was 0.340 g, and the total amount of R-113 injected was 33 ml. Further, nitrogen gas was blown thereinto for 1.5 hours. The desired product was quantitatively analyzed by $^{19}$F-NMR, whereby the yield of the above-identified compound was 78.2%.

$^{19}$F-NMR (376.0 MHz,solvent:CDCl$_3$,standard:CFCl$_3$) δ (ppm): −77.9 (1F),−79.6~−80.8 (1F),−81.1 (3F),−81.2 (3F),−81.8~−82.6 (7F),−85.9~−88.0 (3F),−122.6 (1F),−130.4 (2F), 132.4 and −132.5 (1F).

Example 30

Production of Compound (Ve-51)

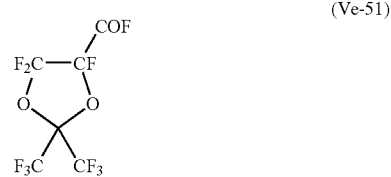

The compound (IVd-51) (1.8 g) obtained in Example 29 was charged into a flask together with a NaF powder (0.02 g), and heated at 120° C. for 12 hours in an oil bath with vigorous stirring. At an upper portion of the flask, a reflux condenser adjusted at the temperature of 20° C., was installed. After cooling, a liquid sample (1.6 g) was recovered. By GC-MS, it was confirmed that CF$_3$CF (OCF$_2$CF$_2$CF$_3$)COF and the above-identified compound were the main products. The NMR spectrum of the above-identified compound agreed to the literature values (J. Chin. Chem. Soc., 40, 563(1993)), and the yield of the above-identified compound was determined by an internal standard method and found to be 73.1%.

Example 31

Production of PhCH$_2$OCH$_2$CH$_2$CH$_2$OCOCF(CF$_3$)OCF$_2$CF$_2$CF$_3$

PhCH$_2$OCH$_2$CH$_2$CH$_2$OH (15 g) having a GC purity of 96%, was put into a flask and stirred while bubbling nitrogen gas. FCOCF(CF$_3$)OCF$_2$CF$_2$CF$_3$ (31.5 g) was added dropwise over a period of 30 minutes while maintaining the internal temperature at from 25 to 30° C. After completion of the dropwise addition, stirring was continued at room temperature for 3 hours, and 50 ml of a saturated sodium hydrogencarbonate aqueous solution was added at an internal temperature of not higher than 15° C.

The obtained crude liquid was subjected to liquid separation, and the lower layer was washed twice with 50 ml of water, dried over magnesium sulfate and then subjected to filtration to obtain a crude liquid. The crude liquid was purified by silica gel column chromatography (developing solvent: AK-225) to obtain PhCH$_2$OCH$_2$CH$_2$CH$_2$OCOCF(CF$_3$)OCF$_2$CF$_2$CF$_3$ (14.2 g). The GC purity was 98%.

$^1$H-NMR (300.4 MHz,solvent:CDCl$_3$,standard:TMS) δ (ppm): 1.98~2.06 (m,2H),3.54 (t,J=6.0 Hz,2H),4.45~4.58 (m,2H),4.49 (s,2H),7.25–7.34 (m,5H).

$^{19}$F-NMR (282.7 MHz,solvent:CDCl$_3$,standard:CFCl$_3$) δ (ppm): −79.9 (1F),−81.3 (3F),−82.2 (3F),−86.5 (1F),−129.5 (2F),−131.5 (1F).

Example 32

Production of Cy$^F$CF$_2$OCF$_2$CF$_2$CF$_2$OCOCF(CF$_3$)OCF$_2$CF$_2$CF$_3$

Into a 500 ml autoclave made of nickel, R-113 (313 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave.

Nitrogen gas was blown thereinto for 1 hour, and then, fluorine gas diluted to 20% with nitrogen gas, was blown thereinto for 1 hour at a flow rate of 8.08 l/hr. Then, while blowing the fluorine gas at the same flow rate, a solution having CyCH$_2$OCH$_2$CH$_2$CH$_2$OCOCF(CF$_3$)OCF$_2$CF$_2$CF$_3$ (4.82 g) obtained in Example 31 dissolved in R-113 (100 g), was injected over a period of 8.4 hours.

Then, while blowing the fluorine gas at the same flow rate and raising the internal pressure of the autoclave to 0.15 MPa, a R-113 solution having a benzene concentration of 0.01 g/ml, was injected in an amount of 6 ml while raising the temperature from 25° C. to 40° C., whereupon the benzene injection inlet of the autoclave was closed, and stirring was continued for 0.3 hour. Then, while maintaining the internal pressure of the reactor at 0.15 MPa and the internal temperature of the reactor at 40° C., 3 ml of the above-mentioned benzene solution was injected, whereupon the benzene injection inlet of the autoclave was closed, and stirring was continued for 0.3 hour. Further, the same operation was repeated three times.

The total amount of benzene injected, was 0.186 g, and the total amount of R-113 injected, was 18 ml. Further, while blowing the fluorine gas at the same flow rate, stirring was continued for 0.8 hour. Then, the internal pressure of the reactor was adjusted to atmospheric pressure, nitrogen gas was blown thereinto for 1.5 hours. The desired product was quantitatively analyzed by $^{19}$F-NMR, whereby the yield of the above-identified compound was 26%.

$^{19}$F-NMR (376.0 MHz,solvent:CDCl$_3$,standard:CFCl$_3$) δ (ppm): −79.9~−84.3 (11F),−87.0~−87.8 (3F),−119.5~−143.5 (10F),−129.8 (2F),−130.5 (2F),−132.5 (1F),−187.9 (1F)

Example 33

Production of Cy$^F$CF$_2$OCF$_2$CF$_2$COF

Cy$^F$CF$_2$OCF$_2$CF$_2$CF$_2$OCOCF(CF$_3$)OCF$_2$CF$_2$CF$_3$ (0.5 g) obtained in Example 32 was charged into a flask together with a NaF powder (0.01 g) and heated at 140° C. for 10 hours in an oil bath with vigorous stirring. At an upper portion of the flask, a reflux condenser adjusted to a temperature of 20° C., was installed. After cooling, a liquid sample (0.4 g) was recovered. From GC-MS, it was confirmed that CF$_3$CF(OCF$_2$CF$_2$CF$_3$)COF (MS(CI method): 495 (M+H)) and the above-identified compound were the main products.

Example 34

Production of CH$_3$CH(OCH$_2$Ph)CH$_2$OCOCF(CF$_3$)OCF$_2$CF$_2$CF$_3$

CH$_3$CH(OCH$_2$Ph)CH$_2$OH (13.1 g) having a GC purity of 96% was put into a flask and stirred while bubbling nitrogen gas. FCOCF(CF$_3$)OCF$_2$CF$_2$CF$_3$ (39.5 g) was added dropwise over a period of 1 hour while maintaining the internal temperature from 25 to 30° C. After completion of the dropwise addition, stirring was continued at room temperature for 3 hours, and 50 ml of a saturated sodium hydrogencarbonate aqueous solution was added at an internal temperature of not higher than 15° C.

The obtained crude liquid was subjected to liquid separation, and the lower layer was washed twice with 50 ml of water, dried over magnesium sulfate and the subjected to filtration to obtain a crude liquid.

The crude liquid was purified by silica gel column chromatography (developing solvent: AK-225) to obtain CH$_3$CH(OCH$_2$Ph)CH$_2$OCOCF(CF$_3$)OCF$_2$CF$_2$CF$_3$ (11 g). The GC purity was 98%.

$^1$H-NMR (300.4 MHz,solvent:CDCl$_3$,standard:TMS) δ (ppm): 1.23 (d,J=6.6 Hz,3H),3.76~3.87 (m,1H),4.26~4.60 (m,2H),4.54,4.56(s,2H),7.26~7.36 (m,5H).

$^{19}$F-NMR (282.7 MHz,solvent:CDCl$_3$,standard:CFCl$_3$) δ (ppm): −80.0 (1F),−81.3 (3F),−82.1 (3F),−86.4 (1F),−129.5 (2F),−131.5 (1F).

Example 35

Production of Cy$^F$CF$_2$OCF(CF$_3$)CF$_2$OCOCF(CF$_3$)OCF$_2$CF$_2$CF$_3$

Into a 500 ml autoclave made of nickel, R-113 (312 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave.

Nitrogen gas was blown thereinto for 1 hour and then, fluorine gas diluted to 20% with nitrogen gas, was blown thereinto for 1 hour at a flow rate of 8.32 l/hr.

Then, while blowing the fluorine gas at the same flow rate, a solution having $CH_3CH(OCH_2Ph)CH_2OCOCF(CF_3)OCF_2CF_2CF_3$ (4.97 g) obtained in Example 34 dissolved in R-113 (100 g), was injected over a period of 8.0 hours.

Then, while blowing the fluorine gas at the same flow rate and raising the internal pressure of the autoclave to 0.15 MPa, a R-113 solution having a benzene concentration of 0.01 g/ml, was injected in an amount of 6 ml while raising the temperature from 25° C. to 40° C., whereupon the benzene injection inlet of the autoclave was closed, and stirring was continued for 0.3 hour. Then, while maintaining the internal pressure of the reactor at 0.15 MPa and the internal temperature of the reactor at 40° C., 3 ml of the above-mentioned benzene solution was injected, whereupon the benzene injection inlet of the autoclave was closed, stirring was continued for 0.3 hour. Further, the same operation was repeated three times.

The total amount of benzene injected was 0.182 g, and the total amount of R-113 injected was 18 ml. Further, while blowing the fluorine gas at the same flow rate, stirring was continued for 0.8 hour. Then, the internal pressure of the reactor was adjusted to atmospheric pressure, and nitrogen gas was blown thereinto for 1.5 hours. The desired product was quantitatively analyzed by $^{19}$F-NMR, whereby the yield of the above-identified compound was 22%.

Example 36

Production of $CH_3CH(OCH_2CH_2CH=CH_2)COOCH_2CH_2CH=CH_2$ $CH_3CHClCOOH$ (50 g) and $CH_2=CHCH_2CH_2OH$ (75 ml) were put into a flask, and 10 ml of concentrated sulfuric acid was added dropwise, followed by stirring at room temperature for 10 minutes. The reaction solution was poured into 250 ml of a saturated sodium carbonate aqueous solution. 150 ml of water and 150 ml of t-butylmethyl ether were added for liquid separation to obtain a t-butylmethyl ether layer as an organic layer. The organic layer was washed with 150 ml of water, dried over magnesium sulfate and then subjected to filtration to obtain a crude liquid. The crude liquid was concentrated to obtain $CH_3CHClCOOCH_2CH_2CH=CH_2$.

$CH_2=CHCH_2CH_2OH$ (16.6 g) and dimethylformamide (120 ml) were put into a flask and cooled so that the internal temperature was maintained at from 8 to 9° C. Sodium hydride (10 g) was added over a period of 30 minutes, and stirring was continued at room temperature of 30 minutes, followed by cooling again. Then, $CH_3CHClCOOCH_2CH_2CH=CH_2$ (50 g) was dissolved in 30 ml of dimethylformamide, which was added dropwise over a period of 1.5 hours. After the dropwise addition, heating was continued for 3 hours while maintaining the internal temperature at from 80 to 85° C. The temperature was returned to room temperature (25° C.), and 200 ml of 2 mol/l hydrochloric acid was added. The mixture was extracted four times with 400 ml of a solution of hexane/ethyl acetate=2/1 to obtain an organic layer. The organic layer was concentrated and then washed twice with 500 ml of water, dried over magnesium sulfate and then subjected to filtration and concentrated again to obtain $CH_3CH(OCH_2CH_2CH=CH_2)COOCH_2CH_2CH=CH_2$ (36 g). The GC purity was 83%.

$^1$H-NMR (399.8 MHz,solvent:CDCl$_3$,standard:TMS) δ (ppm): 1.39 (d,J=7.0 Hz,3H),2.33–2.45 (m,4H),3.41 (dt, J=7.0,9.1 Hz,1H),3.63 (dt,J=7.0,9.1 Hz,1H),3.96 (q,J=7.0 Hz,1H),4.15–4.27 (m,2H),5.02–5.14 (m,4H),5.73–5.88 (m,2H).

Example 37

Production of $CH_3CH(OCH_2CH_2CH=CH_2)CH_2OH$

In an argon atmosphere, lithium aluminum hydride (6.9 g) and 240 ml of dehydrated diethyl ether were put into a flask and stirred in an ice bath. $CH_3CH(OCH_2CH_2CH=CH_2)COOCH_2CH_2CH=CH_2$ (36 g) having a GC purity of 83% obtained in Example 36, was added dropwise thereto over a period of 45 minutes and then stirred at room temperature (25° C.) for 3.5 hours. While cooling in an ice bath, 100 ml of ice water was added dropwise, and 100 ml of water was further added to bring the temperature to room temperature (25° C.), followed by filtration. Washing was carried out with 450 ml of diethyl ether, and the filtrate was subjected to liquid separation. The aqueous layer was further extracted twice with 200 ml of diethyl ether, and the collected diethyl ether layers were obtained as an organic layer. The organic layer was dried over magnesium sulfate and the subjected to filtration to obtain a crude liquid. The crude liquid was concentrated to 35 g and distilled under reduced pressure to remove a fraction (6.6 g) of from 28 to 49° C./9.33 kPa, and from the residue, $CH_3CH(OCH_2CH_2CH=CH_2)CH_2OH$ (19.2 g) was obtained. The GC purity was 98%.

$^1$H-NMR (399.8 MHz,solvent:CDCl$_3$,standard:TMS) δ (ppm): 1.12 (d,J=6.2 Hz,3H),2.35 (tq,J=1.3,6.7 Hz,2H), 3.42–3.48 (m,2H),3.51–3.59 (m,2H),3.64–3.69 (m,1H), 5.04–5.15 (m,2H),5.79–5.89 (m,1H).

Example 38

Production of $CH_3CH(OCH_2CH_2CHClCH_2Cl)CH_2OH$ $CH_3CH(OCH_2CH_2CH=CH_2)CH_2OH$ (19.2 g) having a GC purity of 98% obtained in Example 37, was put into a flask and stirred while bubbling nitrogen gas. Calcium chloride (2.2 g) and water (3.6 g) were added thereto, followed by cooling to 10° C. Chlorine gas was blown thereinto for 2 hours at a supply rate of about 4 g/hr. Then, disappearance of the starting material was confirmed by GC, and diethyl ether (200 ml) and water (200 ml) were added. Liquid separation was carried out, and the organic layer was dried over magnesium sulfate. Then, the solvent was distilled off, and the crude product was used as it was in the step of Example 39.

Example 39

Production of $CH_3CH(OCH_2CH_2CHClCH_2Cl)CH_2OCOCF(CF_3)OCF_2CF_2CF_3$

The crude product of $CH_3CH(OCH_2CH_2CHClCH_2Cl)CH_2OH$ obtained in Example 38 was put into a flask and stirred while bubbling nitrogen gas. $FCOCF(CF_3)OCF_2CF_2CF_3$ (50 g) was added dropwise over a period of 1 hour while maintaining the internal temperature from 25 to 30° C. After completion of the dropwise addition, stirring was continued at room temperature for 3 hours, and 80 ml of a saturated sodium hydrogencarbonate aqueous solution was added at an internal temperature of not higher than 15° C.

50 ml of water and 100 ml of chloroform were added, followed by liquid separation to obtain a chloroform layer as an organic layer. Further, the organic layer was washed twice with 100 ml of water, dried over magnesium sulfate and then subjected to filtration to obtain a crude liquid. The crude liquid was concentrated and then purified by silica gel column chromatography (developing solvent: hexane:ethyl acetate=40:1), and then purified again by silica column chromatography (developing solvent: AK-225) to obtain 37 g of $CH_3CH(OCH_2CH_2CHClCH_2Cl)CH_2OCOCF(CF_3)OCF_2CF_2CF_3$. The GC purity was 88%.

$^1$H-NMR (399.8 MHz,solvent:CDCl$_3$,standard:TMS) δ (ppm): 1.21 (dd,J=1.3,6.3 Hz,3H),1.81–1.93 (m,1H), 2.19–2.26 (m,1H),3.59–3.65 (m,1H),3.68–3.80 (m,4H), 4.20–4.46 (m,3H).

$^{19}$F-NMR (376.2 MHz,solvent:CDCl$_3$,standard:CFCl$_3$) δ (ppm): −80.3 (1F),−81.6 (3F),−82.4 (3F),−86.7 (1F),−130.0 (2F),−132.0 (1F).

Example 40

Production of $CF_2ClCFClCF_2CF_2OCF(CF_3)CF_2OCOCF(CF_3)OCF_2CF_2CF_3$

Into a 500 ml autoclave made of nickel, R-113 (313 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave.

Nitrogen gas was blown thereinto for 1.3 hours, and then fluorine gas diluted to 20% with nitrogen gas, was blown thereinto for 1 hour at a flow rate of 5.77 l/hr. Then, while blowing the fluorine gas at the same flow rate, a solution having $CH_2ClCHClCH_2CH_2OCH(CH_3)CH_2OCOCF(CF_3)OCF_2CF_2CF_3$ (4.63 g) obtained in Example 39 dissolved in R-113 (100 g), was injected over a period of 7.3 hours.

Then, while blowing the fluorine gas at the same flow rate, a R-113 solution having a benzene concentration of 0.01 g/ml, was injected in an amount of 6 ml while raising the temperature from 25° C. to 40° C., whereupon the benzene injection inlet of the autoclave was closed, and further, the outlet valve of the autoclave was closed. When the pressure became 0.20 MPa, the fluorine gas inlet valve of the autoclave was closed, and stirring was continued for 1 hour. Then, the pressure was returned to atmospheric pressure, and while maintaining the internal temperature of the reactor at 40° C., 3 ml of the above-mentioned benzene solution was injected, whereupon the benzene injection inlet of the autoclave was closed, and further, the outlet valve of the autoclave was closed. When the pressure became 0.20 MPa, the fluorine gas inlet valve of the autoclave was closed, and stirring was continued for 1 hour.

Further, the same operation was repeated seven times. The total amount of benzene injected was 0.288 g, and the total amount of R-113 injected was 29 ml. Further, nitrogen gas was blown thereinto for 1.5 hours. The desired product was quantitatively analyzed by $^{19}$F-NMR, whereby the yield of the above-identified compound was 63%.

$^{19}$F-NMR (376.0 MHz,solvent:CDCl$_3$,standard:CFCl$_3$) δ (ppm): −64.7 (2F),−76.5~−80.0 (1F),−80.0~−81.0 (4F),−82.2 (3F),−82.5 (3F),−82.0~−82.9 (1F),−86.4~−88.1 (3F),−117.0~−119.7 (2F),−130.4 (2F),−131.9 (1F),−132.3 (1F),−145.9 (1F).

Example 41

Production of $CH_2=CHCH_2OCH_2CH_2CH_2OCOCF(CF_3)OCF_2CF_2CF_3$ $CH_2=CHCH_2OCH_2CH_2CH_2OH$ (13.9 g) having a GC purity of 99% and triethylamine (25.4 g) were put into a flask and stirred in an ice bath. $FCOCF(CF_3)OCF_2CF_2CF_3$ (41.7 g) was added dropwise over a period of 2 hours while maintaining the internal temperature at a level of not higher than 10° C. After completion of the dropwise addition, stirring was continued at room temperature for 1 hour, and the mixture was added to 50 ml of ice water.

The obtained crude liquid was subjected to liquid separation, and the lower layer was washed twice with 50 ml of water, dried over magnesium sulfate and then subjected to filtration, to obtain a crude liquid. By distillation under reduced pressure, $CH_2=CHCH_2OCH_2CH_2CH_2OCOCF(CF_3)OCF_2CF_2CF_3$ (30.3 g) was obtained as a fraction of from 89 to 90° C./1.2 kPa. The GC purity was 99%.

$^1$H-NMR (300.4 MHz,solvent:CDCl$_3$,standard:TMS) δ (ppm): 1.95~2.03 (m,2H),3.48 (t,J=6.0 Hz,2H),3.94 (dt, J=1.5,6.0 Hz,2H),4.42~4.55 (m,2H),5.16 (d,J=10.5 Hz,1H), 5.24 (d,J=17.1 Hz,1H),5.80~5.93 (m,1H).

$^{19}$F-NMR (282.7 MHz,solvent:CDCl$_3$,standard:CFCl$_3$) δ (ppm): −79.9 (1F),−81.3 (3F),−82.2 (3F),−86.6 (1F),−129.5 (2F),−131.5 (1F).

Example 42

$CF_3CF_2CF_2OCF_2CF_2CF_2OCOCF(CF_3)OCF_2CF_2CF_3$

Into a 500 ml autoclave made of nickel, R-113 (312 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1.0 hour, and then fluorine gas diluted to 20% with nitrogen gas, was blown thereinto for 1 hour at a flow rate of 6.47 l/hr.

Then, while blowing the fluorine gas at the same flow rate, a solution having $CH_2=CHCH_2OCH_2CH_2CH_2OCOCF(CF_3)OCF_2CF_2CF_3$ (4.99 g) obtained in Example 41 dissolved in R-113 (100 g), was injected over a period of 8.0 hours.

Then, while blowing the fluorine gas at the same flow rate, a R-113 solution having a benzene concentration of 0.01 g/ml was injected in an amount of 9 ml while raising the temperature from 25° C. to 40° C., whereupon the benzene injection inlet of the autoclave was closed, and further the outlet valve of the autoclave was closed. When the pressure became 0.20 MPa, the fluorine gas inlet valve of the autoclave was closed, and stirring was continued for 0.6 hour. Then, the pressure was adjusted to atmospheric pressure, and while maintaining the internal temperature of the reactor at 40° C., 6 ml of the above-mentioned benzene solution was injected, whereupon the benzene injection inlet of the autoclave was closed, and further the outlet valve of the autoclave was closed. When the pressure became 0.20 MPa, the fluorine gas inlet valve of the autoclave was closed, and stirring was continued for 0.8 hour. Further, the same operation was repeated once.

The total amount of benzene injected, was 0.219 g and the total amount of R-113 injected was 21 ml. Further, nitrogen gas was blown thereinto for 1.5 hours. The desired product was quantitatively analyzed by $^{19}$F-NMR, whereby the yield of the above-identified compound was 85.8%.

$^{19}$F-NMR (376.0 MHz,solvent:CDCl$_3$,standard: CFCl$_3$) δ (ppm): −79.9 (1F),−82.1 (6F),−82.3 (3F),−83.9 (2F),−84.7 (2F), −86.9 (1F),−87.4 (2F),−129.6 (2F),−130.2 (2F)−130.5 (2F),−132.2 (1F).

Example 43

Production of CF$_3$CF$_2$CF$_2$OCF$_2$CF$_2$COF

CF$_3$CF$_2$CF$_2$OCF$_2$CF$_2$CF$_2$OCOCF(CF$_3$)OCF$_2$CF$_2$CF$_3$ (0.8 g) obtained in Example 42 was charged into a flask together with a NaF powder (0.01 g) and heated at 120° C. for 10 hours in an oil bath with vigorous stirring. At an upper portion of the flask, a reflux condenser adjusted to a temperature of 20° C. was installed. After cooling, a liquid sample (0.7 g) was recovered. By GC-MS, it was confirmed that CF$_3$CF(OCF$_2$CF$_2$CF$_3$)COF and the above-identified compound were the main products. The yield was 57.0%.

$^{19}$F-NMR (376.0 MHz,solvent:CDCl$_3$,standard:CFCl$_3$) δ (ppm): 24.4 (1F),−81.9 (3F),−84.7 (2F),−85.9 (2F),−121.7 (2F),−130.4 (2F).

Example 44

Production of CF$_3$(CF$_3$CF$_2$CF$_2$O)CFCOOCH$_2$CH (OCH$_2$CH$_2$CH$_3$)CH$_3$ and CF$_3$(CF$_3$CF$_2$CF$_2$O)CFCOOCH(CH$_3$)CH$_2$(OCH$_2$CH$_2$CH$_3$)

In a 500 ml four-necked reactor equipped with a Dimroth condenser and dropping funnel, triethylamine (127 ml) was added to a mixture (77.7 g) of 2-propoxy-1-propanol, 1-propoxy-2-propanol and 1-propanol in a ratio of 62:34:4 (molar ratio) obtained by synthesizing from propylene oxide and 1-propanol by a method disclosed in a literature (J. Chem. Soc. Perkin Trans. 2, 199(1993)), followed by distillation under reduced pressure, and the mixture was stirred. FCOCF (CF$_3$)OCF$_2$CF$_2$CF$_3$ (151.4 g) was added dropwise over a period of 1.5 hours while maintaining the internal temperature at a level of not higher than −10° C. After completion of the dropwise addition, stirring was continued at room temperature for 1 hour, and the mixture was added to 400 ml of ice water. AK-225 (400 ml) was added thereto, followed by mixing by shaking, and the mixture was separated by a separating funnel. The organic layer was washed with 400 ml of water and concentrated by an evaporator. The residue (193.1 g) was purified by silica gel column chromatography, followed by distillation to obtain a mixture (90.8 g) of CF$_3$(CF$_3$CF$_2$CF$_2$O)CFCOOCH$_2$CH(OCH$_2$CH$_2$CH$_3$)CH$_3$ and CF$_3$(CF$_3$CF$_2$CF$_2$O)CFCOOCH(CH$_3$)CH$_2$(OCH$_2$CH$_2$CH$_3$) in a ratio of 66.1:33.9 (molar ratio).

Example 45

Production of CF$_3$(CF$_3$CF$_2$CF$_2$O)CFCOOCF$_2$CF (OCF$_2$CF$_2$CF$_3$)CF$_3$ and CF$_3$(CF$_3$CF$_2$CF$_2$O)CFCOOCF(CF$_3$)CF$_2$(OCF$_2$CF$_2$CF$_3$)

Into a 3000 ml autoclave made of nickel, R-113 (1873 g) was added, stirred and maintained at 25° C. At the gas outlet of the autoclave, a condenser maintained at 25° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1.5 hours, and then fluorine gas diluted to 20% with nitrogen gas, was blown thereinto for 3 hours at a flow rate of 8.91 l/hr.

Then, while blowing the fluorine gas at the same flow rate, a solution having the mixture (39.95 g) of CF$_3$(CF$_3$CF$_2$CF$_2$O)CFCOOCH$_2$CH(OCH$_2$CH$_2$CH$_3$)CH$_3$ and CF$_3$(CF$_3$CF$_2$CF$_2$O)CFCOOCH(CH$_3$)CH$_2$(OCH$_2$CH$_2$CH$_3$) obtained in the production of Example 44 dissolved in R-113 (798.8 g), was injected over a period of 42.5 hours.

Then, while blowing the fluorine gas at the same flow rate, a R-113 solution having a benzene concentration of 0.01 g/ml, was injected in an amount of 18 ml while raising the temperature from 25° C. to 40° C., whereupon the benzene injection inlet of the autoclave was closed, and further the outlet valve of the autoclave was closed. When the pressure became 0.20 MPa, the fluorine gas inlet valve of the autoclave was closed, and stirring was continued for 1 hour. Then, the pressure was adjusted to atmospheric pressure, and while maintaining the internal temperature of the reactor at 40° C., 6 ml of the above-mentioned benzene solution was injected, whereupon the benzene injection inlet of the autoclave was closed, and further the outlet valve of the autoclave was closed. When the pressure became 0.20 MPa, the fluorine gas inlet valve of the autoclave was closed, and stirring was continued for 1 hour. Further, the same operation was repeated once. The total amount of benzene injected, was 0.309 g, and the total amount of R-113 injected, was 30 ml. Further, nitrogen gas was blown thereinto for 2.0 hours. The desired product was quantitatively analyzed by $^{19}$F-NMR, whereby the yields of the above-identified compounds were 93% and 91%, respectively.

Example 46

Production of CF$_3$CF(OCF$_2$CF$_2$CF$_3$)COF

CF$_3$CF(OCF$_2$CF$_2$CF$_3$)COOCF$_2$(OCF$_2$CF$_2$CF$_3$)CF$_3$ (6.6 g) obtained in Example 2 was charged into a flask together with a NaF powder (0.13 g) and heated at 120° C. for 4.5 hours and at 140° C. for 2 hours in an oil bath with vigorous stirring. Through a reflux condenser adjusted at a temperature of 70° C., installed at an upper portion of the flask, a liquid sample (5.0 g) was recovered. By GC-MS, it was confirmed that CF$_3$CF(OCF$_2$CF$_2$CF$_3$)COF was the main product. The NMR yield was 72.6%.

Example 47

Production of CF$_3$(CF$_3$CF$_2$CF$_2$O)CFCOOCF$_2$CF (OCF$_2$CF$_2$CF$_3$)CF$_3$ Into a 3000 ml autoclave made of nickel, R-113 (1890 g) was added, stirred and maintained at 25° C. At the gas outlet of the autoclave, a condenser maintained at 20° C., a NaF pellet packed layer and a condenser maintained at −10° C. were installed in series. Further, a liquid returning line was installed to return the condensed liquid from the condenser maintained at −10° C. to the autoclave. Nitrogen gas was blown thereinto for 1.5 hours, and then, fluorine gas diluted to 20% with nitrogen gas, was blown thereinto for 3 hours at a flow rate of 8.91 l/hr.

Then, while blowing the fluorine gas at the same flow rate, a solution having dissolved in R-113 (601 g) CF$_3$(CF$_3$CF$_2$CF$_2$O)CFCOOCH$_2$CH(OCH$_2$CH$_2$CH$_3$)CH$_3$ (60.01 g) synthesized from CF$_3$(CF$_3$CF$_2$CF$_2$O)CFCOF and 2-propoxy-1-propanol obtained by synthesizing from propylene oxide and 1-propanol by a method disclosed in a literature (J. Chem. Soc. Perkin Trans. 2, 199(1993)), followed by purification, was injected over a period of 63.7 hours.

Then, while blowing the fluorine gas at the same flow rate, a R-113 solution having a benzene concentration of 0.01 g/ml, was injected in an amount of 18 ml while raising the temperature from 25° C. to 40° C., whereupon the benzene injection inlet of the autoclave was closed, and further the outlet valve of the autoclave was closed. When the pressure became 0.20 MPa, the fluorine gas inlet valve of the autoclave was closed, and stirring was continued for 1 hour. Then, the pressure was adjusted to atmospheric pressure, and while maintaining the internal temperature of the reactor at 40° C., 6 ml of the above-mentioned benzene solution was injected, whereupon the benzene injection inlet of the autoclave was closed, and further the outlet valve of the autoclave was closed. When the pressure became 0.20 MPa, the fluorine gas inlet valve of the autoclave was closed, and stirring was continued for 1 hour. Further, the same operation was repeated once.

The total amount of benzene injected, was 0.309 g, and the total amount of R-113 injected, was 30 ml. Further, nitrogen gas was blown thereinto for 2.0 hours. After the reaction, distillation purification was carried out to obtain the above-identified compound (86 g).

Example 48

Production of $CF_3CF(OCF_2CF_2CF_3)COF$ $CF_3CF(OCF_2CF_2CF_3)COOCF_2(OCF_2CF_2CF_3)CF_3$ (55.3 g) obtained in Example 47 was charged into a flask together with a NaF powder (0.7 g) and heated at 140° C. for 15 hours in an oil bath with vigorous stirring. Through a reflux condenser adjusted at a temperature of 70° C., installed at an upper portion of the flask, a liquid sample (52.1 g) was recovered. Distillation purification was carried out, and by GC-MS, it was confirmed that $CF_3CF(OCF_2CF_2CF_3)COF$ was the main product. The yield was obtained and found to be 90.4%.

Example 49

Continuous Production Process

Using $CF_3CF(OCF_2CF_2CF_3)COF$ (46.5 g) obtained in Example 48 and 2-propoxy-1-propanol (16.5 g), the reaction was carried out in the same manner as in Example 1 to obtain $CF_3(CF_3CF_2CF_2O)CFCOOCH_2CH(OCH_2CH_2CH_3)CH_3$ (48.0 g).

INDUSTRIAL APPLICABILITY

According to the present invention, it is possible to produce a compound (Ve) which used to be difficult to synthesize or a compound (Ve) which used to be synthesized by an economically disadvantageous method in a short process and in good yield from a compound (Ia). The compound (Ia) is usually readily available and can easily be synthesized and is inexpensive, and compounds of various structures are available. Further, by selecting the structures of $R^A$ and $R^B$ in the compound (Ve), it will be readily soluble in solvent-2 at the time of fluorination, and the fluorination reaction can be proceeded in a liquid phase, whereby the fluorination reaction can be carried out in good yield.

Further, by selecting the structures of $R^A$ and $R^B$, separation of the product (Ve) will be unnecessary. Further, the formed compound (Ve) can be recycled as a compound (IIb) again for the reaction with the compound (Ia), whereby the compound (Ve) can be produced by a continuous process. Further, according to the present invention, a novel compound useful as a fluorine resin material will be provided.

What is claimed is:

1. A process for producing a fluorine-containing compound, which comprises:
   reacting compound (Ia) with compound (IIb) to form compound (IIIc);
   fluorinating compound (IIIc) with fluorine gas in a liquid phase to form compound (IVd) by one of the following two methods:
   i) reacting compound (IIIc) with fluorine gas in a solvent medium in the presence of a C—H bond containing compound, or
   ii) reacting compound (IIIc) with fluorine gas in a solvent medium with exposure to UV radiation; and then
   converting compound (IVd) to compound (Ve) and/or compound (VIf), wherein the fluorine content in compound (Ia) is less than 10 wt %, and the fluorine content in compound (IIIc) ranges from 30 to 76 wt %:

wherein $R^A$, $R^B$: each independently is a monovalent saturated hydrocarbon group, a halogeno-monovalent saturated hydrocarbon group, a hetero atom-containing monovalent saturated hydrocarbon group, a halogeno (hetero atom-containing monovalent saturated hydrocarbon) group, or a monovalent organic group ($R^H$) which can be converted to $R^{HF}$ by a fluorination reaction in a liquid phase,
   $R^{HF}$ is a group having at least one hydrogen atom in a group selected from the group consisting of a monovalent saturated hydrocarbon group, a partially halogeno-monovalent saturated hydrocarbon group, a hetero atom-containing monovalent saturated hydrocarbon group, and a partially halogeno-(hetero atom-containing monovalent hydrocarbon) group, substituted by a fluorine atom;
   $R^{AF}$, $R^{BF}$: $R^{AF}$ is a group corresponding to $R^A$, and $R^{BF}$ is a group corresponding to $R^B$; and in the instance where each of $R^A$ and $R^B$ is a monovalent saturated hydrocarbon group, a halogeno monovalent saturated hydrocarbon group, a hetero atom-containing monovalent saturated hydrocarbon group, or a halogeno (hetero atom-containing saturated hydrocarbon) group, $R^{AF}$ and $R^{BF}$ are the same groups as $R^A$ and $R^B$, respectively, or groups having at least one hydrogen atom present in the groups of $R^A$ and $R^B$ substituted by a fluorine atom, and in the case where $R^A$ and $R^B$ are monovalent organic groups ($R^H$), $R^{AF}$ and $R^{BF}$ are $R^{HF}$, respectively; and
   X is a halogen atom.

2. The process according to claim 1, wherein $R^A$ is a group which does not contain fluorine atoms, and $R^B$ is a group which contains a fluorine atom.

3. The process according to claim 1, wherein the fluorination in the liquid phase perfluorinates compound (IIIc).

4. The process according to claim 1, wherein each of $R^{AF}$ and $R^{BF}$ is a perfluoro monovalent saturated hydrocarbon group, a perfluoro (partially halogeno monovalent saturated hydrocarbon) group, a perfluoro (hetero atom-containing monovalent saturated hydrocarbon) group, or a perfluoro {partially halogeno (hetero atom-containing monovalent saturated hydrocarbon)} group.

5. The process according to claim 1, wherein $R^{AF}$ is the same as $R^{BF}$.

6. The process according to claim 1, wherein compound (VIf), formed by the conversion of compound (IVd), is used as compound (IIb).

7. The process according to claim 1, wherein the conversion reaction of compound (IVd) is a decomposition reaction by heat, or a dissociation reaction conducted in a liquid phase in the presence of a nucleophile or an electrophile.

8. The process according to claim 1, wherein the conversion reaction of compound (IVd) is conducted in a liquid phase in the absence of a solvent in the presence of a fluoride anion derived from an alkali metal fluoride.

9. The process according to claim 1, wherein compound (Ia) is the following compound (Ia-2), compound (IIb) is the following compound (IIb-2), compound (IIIc) is the following compound (IIIc-2), compound (IVd) is the following compound (IVd-2), compound (Ve) is the following compound (Ve-2), and compound (VIf) is the following compound (IIb-2):

$R^1CH_2OH$ (Ia-2)

$FCOR^2$ (IIb-2)

$R^1CH_2OCOR^2$ (IIIc-2)

$R^3CF_2OCOR^2$ (IVd-2)

$R^3COF$ (Ve-2)

wherein $R^1$ is an alkyl group, an alkoxyalkyl group, a halogenoalkyl group or a halogeno(alkoxyalkyl) group;

$R^2$ is a perhalogenoalkyl group, or a perhalogeno(alkoxyalkyl) group; and $R^3$ is a group that corresponds to $R^1$; and when $R^1$ is a group that does not contain a hydrogen atom, it is the same group as $R^1$ and when $R^1$ is a group that contains hydrogen atoms, it is a group that has all of its hydrogen atoms in said group substituted by fluorine atoms.

10. The process according to claim 9, wherein $R^1$ is a group which does not contain fluorine atoms, and $R^2$ is a group which contains a fluorine atom.

11. The process according to claim 9, wherein the fluorination in the liquid phase perfluorinates compound (IIIc-2).

12. The process according to claim 9, wherein each of $R^2$ and $R^3$ is a perfluoro monovalent saturated hydrocarbon group, a perfluoro (partially halogeno monovalent saturated hydrocarbon) group, a perfluoro (hetero atom-containing monovalent saturated hydrocarbon) group, or a perfluoro {partially halogeno (hetero atom-containing monovalent saturated hydrocarbon)} group.

13. The process according to claim 9, wherein $R^2$ is the same as $R^3$.

14. The process according to claim 9, wherein compound (VIf-2), formed by the conversion of compound (IVd-2), is used as compound (IIb-2).

15. The process according to claim 9, wherein the conversion reaction of compound (IVd-2) is a decomposition reaction by heat, or a dissociation reaction conducted in a liquid phase in the presence of a nucleophile or an electrophile.

16. A process for producing a fluorine-containing compound, which comprises:

reacting compound (Ia) with compound (IIb) to form compound (IIIc);

fluorinating compound (IIIc) with fluorine gas in a liquid phase to form compound (IVd) by one of the following two methods;

i) reacting compound (IIIc) with fluorine gas in a solvent medium in the presence of a C—H bond containing compound, or ii) reacting compound (IIIc) with fluorine gas in a solvent medium with exposure to UV radiation; and then converting compound (IVd) to compound (Ve) and/or compound (VIf), wherein the conversion reaction of compound (IVd) is conducted in a liquid phase in the absence of a solvent in the presence of a fluoride anion derived from an alkali metal fluoride:

$R^ACH_2OH$ (Ia)

$XCOR^B$ (IIb)

$R^ACH_2OCOR^B$ (IIIc)

$R^{AF}CF_2OCOR^{BF}$ (IVd)

$R^{AF}COF$ (Ve)

$R^{BF}COF$ (VIf)

wherein $R^A$, $R^B$: each independently is a monovalent saturated hydrocarbon group, a halogeno-monovalent saturated hydrocarbon group, a hetero atom-containing monovalent saturated hydrocarbon group, a halogeno (hetero atom-containing monovalent saturated hydrocarbon) group, or a monovalent organic group ($R^H$) which can be converted to $R^{HF}$ by a fluorination reaction in a liquid phase, $R^{HF}$ is a group having at least one hydrogen atom in a group selected from the group consisting of a monovalent saturated hydrocarbon group, a partially halogeno-monovalent saturated hydrocarbon group, a hetero atom-containing monovalent saturated hydrocarbon group, and a partially halogeno-(hetero atom-containing monovalent hydrocarbon) group, substituted by a fluorine atom;

$R^{AF}$, $R^{BF}$: $R^{AF}$ is a group corresponding to $R^A$, and $R^{BF}$ is a group corresponding to $R^B$; and in the instance where each of $R^A$ and $R^B$ is a monovalent saturated hydrocarbon group, a halogeno monovalent saturated hydrocarbon group, a hetero atom-containing monovalent saturated hydrocarbon group, or a halogeno (hetero atom-containing monovalent saturated hydrocarbon) group, $R^{AF}$ and $R^{BF}$ are the same groups as $R^A$ and $R^B$, respectively, or groups having at least one hydrogen atom present in the groups of $R^A$ and $R^B$ substituted by a fluorine atom, and in the case where $R^A$ and $R^B$ are monovalent organic groups ($R^H$), $R^{AF}$ and $R^{BF}$ are $R^{HF}$, respectively; and X is a halogen atom.

* * * * *